United States Patent
Matsunaga et al.

(10) Patent No.: US 11,859,212 B2
(45) Date of Patent: Jan. 2, 2024

(54) METHOD FOR PRODUCING INTESTINAL ORGANOID DERIVED FROM PLURIPOTENT STEM CELLS

(71) Applicant: PUBLIC UNIVERSITY CORPORATION NAGOYA CITY UNIVERSITY, Nagoya (JP)

(72) Inventors: Tamihide Matsunaga, Nagoya (JP); Takahiro Iwao, Nagoya (JP); Daichi Onozato, Nagoya (JP); Isamu Ogawa, Nagoya (JP)

(73) Assignee: PUBLIC UNIVERSITY CORPORATION NAGOYA CITY UNIVERSITY, Nagoya (JP)

( * ) Notice: Subject to any disclaimer, the term of this patent is extended or adjusted under 35 U.S.C. 154(b) by 841 days.

(21) Appl. No.: 16/611,359

(22) PCT Filed: May 2, 2018

(86) PCT No.: PCT/JP2018/017572
§ 371 (c)(1),
(2) Date: Nov. 6, 2019

(87) PCT Pub. No.: WO2018/207714
PCT Pub. Date: Nov. 15, 2018

(65) Prior Publication Data
US 2020/0157507 A1 May 21, 2020

(30) Foreign Application Priority Data
May 9, 2017 (JP) .................. 2017-093418

(51) Int. Cl.
C12N 5/071 (2010.01)
G01N 33/50 (2006.01)
A61L 27/38 (2006.01)

(52) U.S. Cl.
CPC ........ *C12N 5/0679* (2013.01); *A61L 27/3834* (2013.01); *A61L 27/3882* (2013.01);
(Continued)

(58) Field of Classification Search
CPC .............. C12N 5/0679; C12N 2513/00; C12N 2501/11; C12N 2501/115;
(Continued)

(56) References Cited

U.S. PATENT DOCUMENTS

2013/0137130 A1 5/2013 Wells et al.
2015/0140661 A1 5/2015 Toyoshima et al.
(Continued)

FOREIGN PATENT DOCUMENTS

CN 104428410 A 3/2015
EP 2636731 B1 9/2013
(Continued)

OTHER PUBLICATIONS

Van Dussen et al. "Notch signaling modulates proliferation and differentiation of intestinal crypt base columnar stem cells" Development Feb. 1, 2012; 139(3): 488-497. (Year: 2012).*
(Continued)

*Primary Examiner* — Marcia S Noble
*Assistant Examiner* — Lauren K Van Buren
(74) *Attorney, Agent, or Firm* — Locke Lord LLP

(57) ABSTRACT

An object of the present invention is to prepare a functional intestinal organoid from pluripotent stem cells. An intestinal organoid is prepared from pluripotent stem cells, by the following steps (1) to (4): (1) differentiating pluripotent stem cells into endoderm-like cells; (2) differentiating the endoderm-like cells obtained in step (1) into intestinal stem cell-like cells; (3) culturing the intestinal stem cell-like cells obtained in step (2) to form spheroids; and (4) differentiating the spheroids formed in step (3) to form an intestinal (Continued)

organoid, the step including culture in the presence of a MEK1/2 inhibitor, a DNA methylation inhibitor, a TGF-β receptor inhibitor, and a γ-secretase inhibitor, in addition to an epidermal growth factor, a BMP inhibitor, and a Wnt signal activator.

14 Claims, 25 Drawing Sheets

(52) U.S. Cl.
CPC ...... *A61L 27/3895* (2013.01); *G01N 33/5082* (2013.01); *C12N 2501/11* (2013.01); *C12N 2501/115* (2013.01); *C12N 2501/119* (2013.01); *C12N 2501/998* (2013.01); *C12N 2501/999* (2013.01); *C12N 2503/04* (2013.01); *C12N 2506/45* (2013.01); *C12N 2513/00* (2013.01); *C12N 2533/70* (2013.01)

(58) Field of Classification Search
CPC ........ C12N 2501/119; C12N 2501/998; C12N 2501/999; C12N 2503/04; C12N 2506/45; C12N 2533/70; G01N 33/5082; A61L 27/3834; A61L 27/3882; A61L 27/3895
See application file for complete search history.

(56) References Cited

U.S. PATENT DOCUMENTS

| | | | |
|---|---|---|---|
| 2015/0201588 A1* | 7/2015 | Kamb | C12N 5/0679 435/6.12 |
| 2017/0292116 A1 | 10/2017 | Wells et al. | |
| 2017/0335277 A1 | 11/2017 | Takebe et al. | |
| 2017/0362573 A1* | 12/2017 | Wells | C12N 5/0661 |
| 2018/0030409 A1 | 2/2018 | Lewis et al. | |

FOREIGN PATENT DOCUMENTS

| | | | | |
|---|---|---|---|---|
| EP | 2718422 A2 | 4/2014 | | |
| EP | 3239294 A1 | 11/2017 | | |
| EP | 2857500 B1 | 1/2018 | | |
| JP | 2006-239169 A | 9/2006 | | |
| JP | 6296399 B2 | 3/2018 | | |
| WO | 2010/143747 A1 | 12/2010 | | |
| WO | 2012/060315 A1 | 5/2012 | | |
| WO | 2013/176249 A1 | 11/2013 | | |
| WO | 2014/132933 A1 | 9/2014 | | |
| WO | WO-2014132933 A1 * | 9/2014 | | C12N 5/0679 |
| WO | 2016/061464 A1 | 4/2016 | | |
| WO | 2016/093222 A1 | 6/2016 | | |
| WO | 2016/125884 A1 | 8/2016 | | |
| WO | 2016/141137 A1 | 9/2016 | | |
| WO | WO-2016141137 A1 * | 9/2016 | | A61K 35/545 |

OTHER PUBLICATIONS

Gasperini et al. "Natural polymers for the microencapsulation of cells" Journal of the Royal Society Interface (Year: 2014).*
Yin et al. "Niche-independent high-purity cultures of Lgr5+ intestinal stem cells and their progeny" Nature Methods, vol. 11, No. 1, Jan. 2014, p. 106 (Year: 2014).*
Office Action dated Oct. 10, 2022, issued in the corresponding Chinese patent application No. 201880030351.3 with its English Machine Translation.
Kelli L. VanDussen et al., "Notch signaling modulates proliferation and differentiation of intestinal crypt base columnar stem cells," Development and Stem Cells, 139, 2012, pp. 488-497.
Soichiro Ogaki et al., "Wnt and Notch Signals Guide Embryonic Stem Cell Differentiation into the Intestinal lineages," Stem Cells, vol. 31, No. 6, Jun. 22, 2013, pp. 1086-1096. (cited in the Dec. 18, 2020 Search Report issued for EP18799226.8).
Kai Liu et al., "Chemical Modulation of Cell Fate in Stem Cell Therapeutics and Regenerative Medicine," Cell Chemical Biology, Elsevier, Amsterdam, NL, vol. 23, No. 8, Aug. 11, 2016, pp. 893-916. (cited in the Dec. 18, 2020 Search Report issued for EP18799226.8).
Daichi Onozato et al., "Generation of Intestinal Organoids Suitable for Pharmacokinetic Studies from Human Induced Pluripotent Stem Cells," Drug Metabolism and Disposition, vol. 46, No. 11, Apr. 3, 2018, pp. 1572-1580. (cited in the Dec. 18, 2020 Search Report issued for EP18799226.8).
Extended European Search Report dated Dec. 18, 2020, issued in the corresponding European patent application No. 18799226.8.
T. Iwao et al., "Differentiation of Human Induced Pluripotent Stem Cells into Functional Enterocyte-like Cells Using a Simple Method," Drug Metab. Pharmacokinet, 29(1), 2014, pp. 44-51. (cited in the ISR and discussed in the spec).
J. R. Spence et al., "Directed differentiation of human pluripotent stem cells into intestinal tissue in vitro," Nature, 470(7332), Feb. 3, 2011, pp. 105-109. (discussed in the spec).
S. Torihashi et al., "Gut-Like Structures from Mouse Embryonic Stem Cells as an In Vitro Model for Gut Organogenesis Preserving Developmental Potential After Transplantation," Stem Cells, 24, 2006, pp. 2618-2626. (discussed in the spec).
T. Ueda et al., "Generation of functional gut-like organ from mouse induced pluripotent stem cells," Biochem. Biophys. Res. Commun., 391(1), 2010, pp. 38-42. (discussed in the spec).
N. Kodama et al., "Inhibition of mitogen-activated protein kinase kinase, DNA methyltransferase, and transforming growth factor-beta promotes differentiation of human induced pluripotent stem cells into enterocytes," Drug Metab. Pharmacokinet, 31, 2016, 193-200. (cited in the ISR).
L. Cao et al., "Development of Intestinal Organoids as Tissue Surrogates: Cell Composition and the Epigenetic Control of Differentiation," Molecular Carcinogenesis, 54, 2015, pp. 189-202. (cited in the ISR).
K. W. McCracken et al., "Generating human intestinal tissue from pluripotent stem cells in vitro," Nature Protocols, 6(12), 2011, pp. 1920-1928. (cited in the ISR).
International Search Report dated Aug. 7, 2018, issued for PCT/JP2018/017572.
Office Action dated Jan. 30, 2023, issued in the corresponding Korean patent application No. 10-2019-7033665 with its English Machine Translation.
Office Action dated Feb. 11, 2023, issued in the corresponding Chinese patent application No. 201880030351.3 with its English Machine Translation.
Office Action dated Apr. 26, 2022, issued in the corresponding Japanese patent application No. 2019-517600 with its English Machine Translation.
Decision on Rejection dated Sep. 23, 2023, issued in the corresponding Chinese patent application No. 201880030351.3 with its English Machine Translation.

* cited by examiner

A

| Day 0 | Day 3 | Day 7 | Day 10 | Day 19 | Day 34 |

|  | | EZ SPHERE | | Low molecular weight compound | |
| Activin A (100 ng/mL) | FGF4 (500 ng/mL) + Wnt3a (500ng/mL) | R-spondin 1 (200 ng/mL) +Noggin (100 ng/mL) +EGF (100 ng/mL) | | | |

B

| Day 0 | Day 3 | Day 7 | Day 10 | Day 19 | Day 34 |

|  | CHIR99021 (6 µM) | EZ SPHERE | | Low molecular weight compound | |
| Activin A (100 ng/mL) | FGF2 (250 ng/mL) | R-spondin 1 (200 ng/mL) +Noggin (100 ng/mL) +EGF (100 ng/mL) | | | |

*Fig. 9*

METHOD FOR PRODUCING INTESTINAL ORGANOID DERIVED FROM PLURIPOTENT STEM CELLS

TECHNICAL FIELD

The present invention relates to a method for preparing an intestinal organoid derived from pluripotent stem cells and uses thereof. The present application claims priority based on Japanese Patent Application No. 2017-093418 filed on May 9, 2017, the entire contents of which are incorporated herein by reference.

BACKGROUND ART

The small intestine is a very important organ in considering the pharmacokinetics of orally administered drugs. In order to comprehensively evaluate the pharmacokinetics (absorption, excretion, metabolism) in the human small intestine at the stage of non-clinical studies, it is desirable to use primary small intestinal epithelial cells, but the cells are difficult to obtain. In recent years, three-dimensional tissue structures (organoid) that mimic intestinal tissue have attracted attention as novel in vitro evaluation systems. However, an intestinal organoid differentiated from embryonic stem cells (ES cells) or induced pluripotent stem cells (iPS cells), which that have the same pluripotency as that of ES cells and almost unlimited proliferative potential and are expected to be used for drug discovery research, are immature, and their pharmacokinetic functions have been hardly analyzed.

In addition, mammals other than humans are useful for disease models and biomedical research. In particular, a cynomolgus monkey used as an experimental animal in drug discovery research has quite many similarities to human, and the amino acid sequences of drug-metabolizing enzymes and transporters are 90 to 95% homologous and similar in substrate specificity. Therefore, it is possible to predict the pharmacokinetics in humans more accurately by confirming in vivo and in vitro correlation using a cynomolgus monkey at the stage of non-clinical studies.

It has been reported that intestinal epithelial cells were prepared from ES cells and iPS cells in two-dimensional (2D) culture (see, for example, PTLs 1 and 2), and that intestinal organoids were prepared in three-dimensional (3D) culture using Matrigel and the like (for example, PTLs 3 and 4 and NPLs 1 to 4).

CITATION LIST

Patent Literature

[PTL 1] WO 2014/132933
[PTL 2] WO 2012/060315
[PTL 3] WO 2016/093222
[PTL 4] JP 2006-239169 A

Non Patent Literature

[NPL 1] Drug Metab. Pharmacokinetic Vol. 29 (1). P. 44-51 (2014)
[NPL 2] Nature, Vol. 470, P. 105-109 (2011)
[NPL 3] Stem Cells, vol. 24, P. 2618-2626 (2006)
[NPL 4] Biochem. Biophys. Res. Commun., Vol. 391 (1), No. 7, P. 38-42 (2010)

SUMMARY OF INVENTION

Technical Problem

The intestinal epithelial cells obtained in 2D culture as described above are difficult to culture for a long time. Moreover, they do not form intestinal organoids, and the evaluation systems using them differ from the case of intestinal organoids in terms of configuration, use, utility value, and the like. On the other hand, the functionality of the intestinal organoids prepared by 3D culture has not been sufficiently verified (which probably seem to be immature structures), that is, their practicality is unknown, and it is hard to say that they can be utilized, for example, for analysis of pharmacokinetics. Therefore, a first problem of the present invention is to prepare a functional (that is, having a pharmacokinetic function) intestinal organoid from pluripotent stem cells, and a second problem thereof is to improve the intestinal organoid preparation efficiency.

Solution to Problem

As a result of intensive studies to solve the above problems, the present inventors have found a combination of factors effective for the formation of the functional intestinal organoid. A functional tight junction has been observed in the intestinal organoid that was successfully formed, and the transport function of an efflux transporter, the drug metabolizing enzyme activity, and the like have also been confirmed. The achievements of the present inventors are different from past reports also in that it has been demonstrated that a functional intestinal organoid having a pharmacokinetic function can be constructed. On the other hand, the intestinal organoid preparation efficiency has been successfully enhanced by improving the culture method. In addition, all of the factors adopted in the novel combination are low molecular weight compounds that are inexpensive and have little lot-to-lot difference. This feature brings about improvements in quality and reliability of the intestinal organoid in addition to reduction in cost for preparing the intestinal organoid.

Further studies have found a preparation method that is particularly advantageous when applied to regenerative medicine.

The following inventions are mainly based on the above results.

[1] A method for preparing an intestinal organoid from pluripotent stem cells, including the following steps (1) to (4):
 (1) differentiating pluripotent stem cells into endoderm-like cells;
 (2) differentiating the endoderm-like cells obtained in step (1) into intestinal stem cell-like cells;
 (3) culturing the intestinal stem cell-like cells obtained in step (2) to form spheroids; and
 (4) differentiating the spheroids formed in step (3) to form an intestinal organoid, the step including culture in the presence of a MEK1/2 inhibitor, a DNA methylation inhibitor, a TGF-β receptor inhibitor, and a γ-secretase inhibitor, in addition to an epidermal growth factor, a BMP inhibitor, and a Wnt signal activator.

[2] The preparation method according to [1], in which the pluripotent stem cells are induced pluripotent stem cells or embryonic stem cells.

[3] The preparation method according to [1] or [2], in which the pluripotent stem cells are human or primate cells.

[4] The preparation method according to [1], in which the pluripotent stem cells are human induced pluripotent stem cells, and in which step (2) includes culture in the presence of FGF4 and a Wnt agonist.

[5] The preparation method according to [4], in which the human induced pluripotent stem cells are induced pluripotent stem cells derived from a patient with a bowel disease.

[6] The preparation method according to [1], in which the pluripotent stem cells are cynomolgus monkey induced pluripotent stem cells, and in which step (2) includes culture in the presence of FGF2 and a GSK-3 inhibitor.

[7] The preparation method according to any one of [1] to [6], in which, in the culture in step (3), a plurality of the spheroids are formed together by using a culture vessel in which a plurality of wells uniform in shape and size are formed in a low cell adhesive or non-cell adhesive culture surface.

[8] The preparation method according to any one of [1] to [7], in which the BMP inhibitor is Noggin, and in which the Wnt signal activator is R-spondin-1. [9] The preparation method according to any one of [1] to [8], in which the MEK1/2 inhibitor is PD98059, in which the DNA methylation inhibitor is 5-aza-2'-deoxycytidine, in which the TGF-β receptor inhibitor is A-83-01, and in which the γ-secretase inhibitor is N-[(3,5-difluorophenyl)acetyl]-L-alanyl-2-phenyl-1,1-dimethylethyl ester-glycine.

[10] The preparation method according to any one of [1] to [9], in which a liquid medium to which a material that is able to form a three-dimensional network structure in an aqueous solution is added is used for the culture in step (4), and in which a plurality of the spheroids formed in step (3) are cultured together in suspension.

[11] The preparation method according to [10], in which the material is one or more materials selected from the group consisting of polymer gels and polysaccharides. [12] The preparation method according to [10], in which the material includes deacylated gellan gum.

[13] The preparation method according to any one of [1] to [12], in which the culture period in step (4) is 12 days to 36 days.

[14] The preparation method according to any one of [1] to [12], in which step (4) includes the following steps (4-1) and (4-2):

(4-1) culture in the presence of the epidermal growth factor, the BMP inhibitor, and the Wnt signal activator; and
(4-2) culture in the presence of the MEK1/2 inhibitor, the DNA methylation inhibitor, the TGF-β receptor inhibitor, and the γ-secretase inhibitor, in addition to the epidermal growth factor, the BMP inhibitor, and the Wnt signal activator.

[15] The preparation method according to [14], in which the culture period in step (4-1) is 3 days to 15 days, and in which the culture period in step (4-2) is 3 days to 21 days.

[16] An intestinal organoid obtained by the preparation method according to any one of [1] to [15].

[17] A method for evaluating pharmacokinetics or toxicity of a test substance using the intestinal organoid according to [16].

[18] The evaluation method according to [17], in which the pharmacokinetics is metabolism, absorption, membrane permeability, drug interaction, drug metabolizing enzyme induction, or drug transporter induction.

[19] The method according to [18], including the following steps (I) and (II):

(I) bringing the test substance into contact with the intestinal organoid according to [16]; and (II) measuring/evaluating the metabolism, absorption, membrane permeability, drug interaction, drug metabolizing enzyme induction, drug transporter induction, or toxicity of the test substance.

[20] A transplantation material including the intestinal organoid according to [16].

BRIEF DESCRIPTION OF DRAWINGS

FIG. 1-2 Continuation of FIG. 1.
FIG. 1-3 Continuation of FIG. 1.
FIG. 1-4 Continuation of FIG. 1.
FIG. 1-5 Continuation of FIG. 1.
FIG. 1-6 Continuation of FIG. 1.
FIG. 1-7 Continuation of FIG. 1.

FIG. 2 Morphological observation of human and cynomolgus monkey intestinal organoids obtained by differentiation induction using a novel combination of low molecular weight compounds. (A), (B): Bright field observation. Scale bar 500 μm. (C), (D): Observation of microvilli (MV: tip of a black arrow) and tight junctions (TJ: tip of a white arrow) with a transmission electron microscope. Scale bar 1 μm. (E)-(G): HE staining. Scale bar 100 μm. (H)-(J): Alcian blue staining (black arrow). Scale bar 100 μm.

FIG. 3 Immunofluorescence staining of the human and cynomolgus monkey intestinal organoids obtained by differentiation induction using the novel combination of low molecular weight compounds. (A)-(C): Villin/OLFM4. (D)-(F): E-cad (epithelial cell adhesion factor)/MUC2. (G)-(I): E-cad/CHGA (Chromogranin A). (J)-(L): E-cad/Lyso (Lysozyme). (M)-(O): Vim (Vimentin: fibroblast marker)/α-SMA (smooth muscle marker). DAPI: Nuclear staining. Scale bar 50 μm.

FIG. 4 Formation of functional tight junctions of the human and cynomolgus monkey intestinal organoids obtained by differentiation induction using the novel combination of low molecular weight compounds. (A)-(C): Occludin immunofluorescence staining. DAPI: Nuclear staining. Scale bar 50 μm. (D)-(G): An uptake test with FITC-dextran 4000 (FD-4). FD-4 (1 mg/mL) was incubated at 37° C. for 1 hour. (D), (E): Bright field observation. (F), (G): Fluorescence observation of FD-4. Scale bar 100 μm.

FIG. 5 Immunostaining of transporters of the human and cynomolgus monkey intestinal organoids obtained by differentiation induction using the novel combination of low molecular weight compounds. (A)-(C): Immunofluorescent staining of SLC15A1/PEPT1. (D)-(F): Immunofluorescent staining of ABCB1/MDR1. DAPI: Nuclear staining. (A)-(E): Scale bar 50 μm. (F): Scale bar 100 μm.

FIG. 6 Evaluation of the function of ABCB1/MDR1 using rhodamine 123 of the human intestinal organoids obtained by differentiation induction using the novel combination of low molecular weight compounds. Rhodamine 123 (10 μmol/L) was added in the absence (A, B) and presence (C, D) of verapamil (100 μmol/L), an inhibitor of ABCB1/MDR1, and the mixture was incubated at 37° C. for 1 hour. Scale bar 100 μm.

FIG. 7 CYP3A induction ability of the human and cynomolgus monkey intestinal organoids obtained by differentiation induction using the novel combination of low molecular weight compounds. Mean±S.D. (n=3); control;

group to which no inducer was added. **P<0.01, *P<0.05 vs control group (human) †P<0.05 vs control group (cynomolgus monkey).

Figure 8:
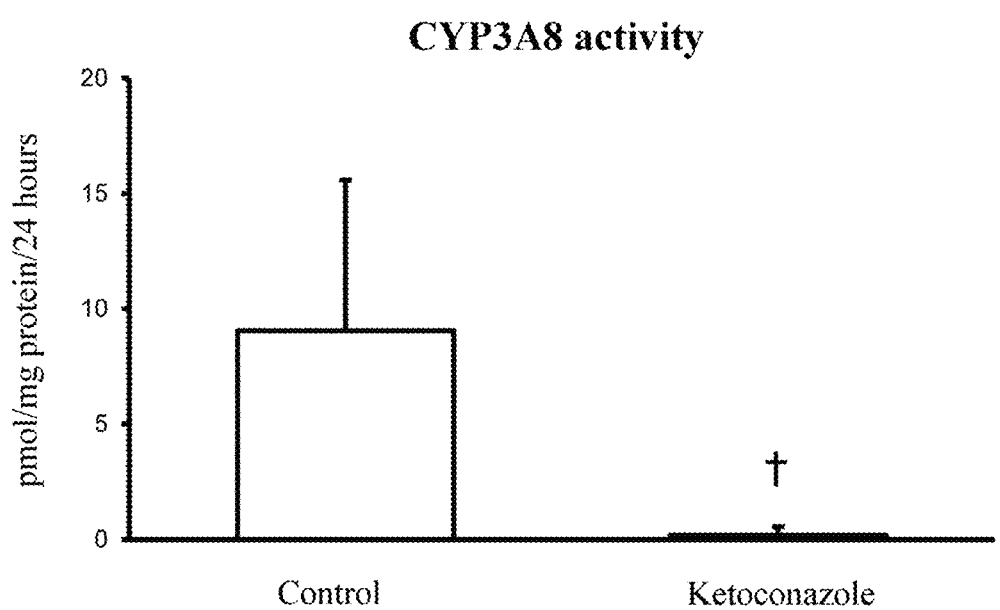

FIG. 8 CYP3A8 metabolic activity of the cynomolgus monkey intestinal organoids obtained by differentiation induction using the novel combination of low molecular weight compounds. Mean±S.D. (n=4); control; group to which no ketoconazole was added. †P 0.05 vs control group (cynomolgus monkey).

FIG. 9 A novel differentiation protocol from induced pluripotent stem cells to intestinal organoids. (A) Differentiation protocol from human iPS cells to intestinal organoids. (B) Differentiation protocol from iPS cells of a cynomolgus monkey to intestinal organoids. The following two types of combinations of low molecular weight compounds were compared/examined Group to which A/PD/5-aza: A-83-01 (0.5 µmol/L), PD98059 (20 µmol/L), and 5-aza-2'-deoxycytidine (5 µmol/L) were added. Group to which A/PD/5-aza/DAPT: A-83-01 (0.5 µmol/L), PD98059 (20 µmol/L), 5-aza-2'-deoxycytidine (5 µmol/L), and DAPT (5 µmol/L) were added.

Figure 1:
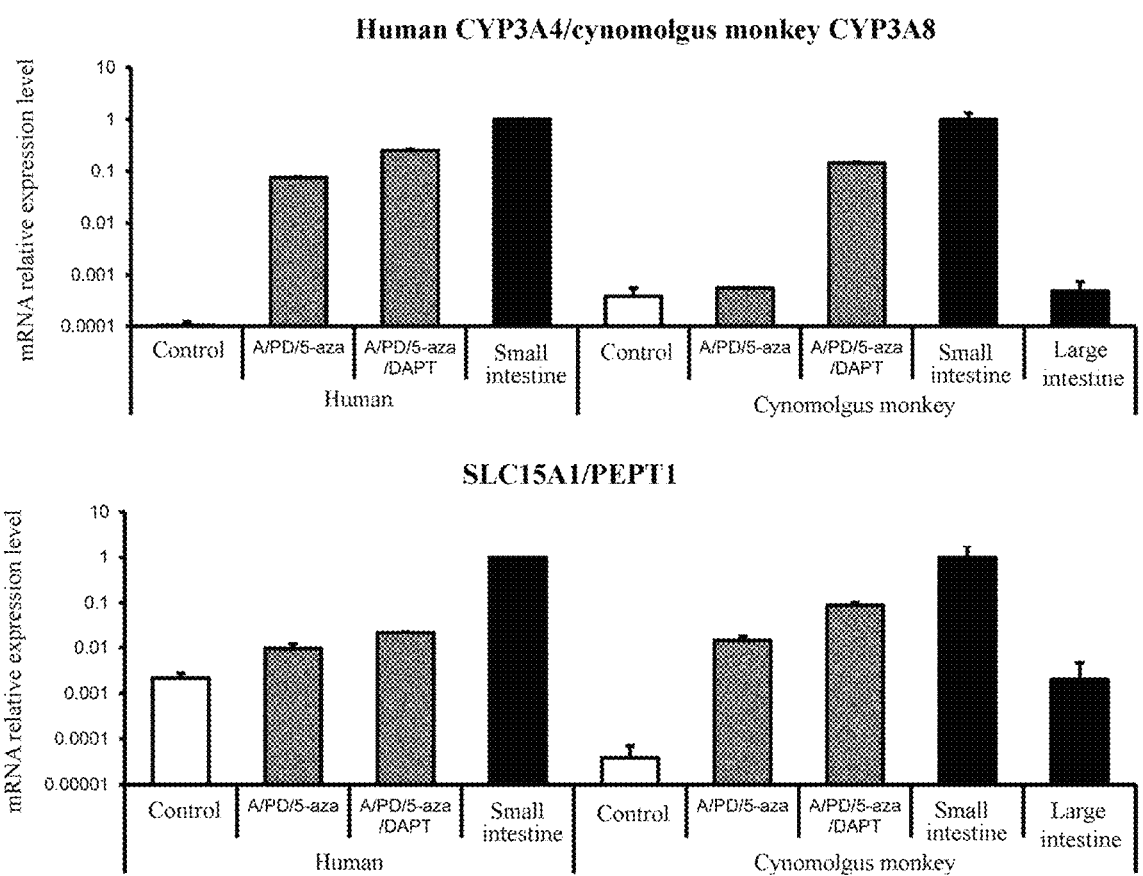
FIG. 1-1 Effects of a low molecular weight compound on differentiation from human and cynomolgus monkey iPS cells into intestinal organoids. Data is shown as mean±S.D. (n=3). A group to which no low molecular weight compound was added was used as a control. The value for the small intestine was used as a reference (small intestine=1).
Figures 1, 2:
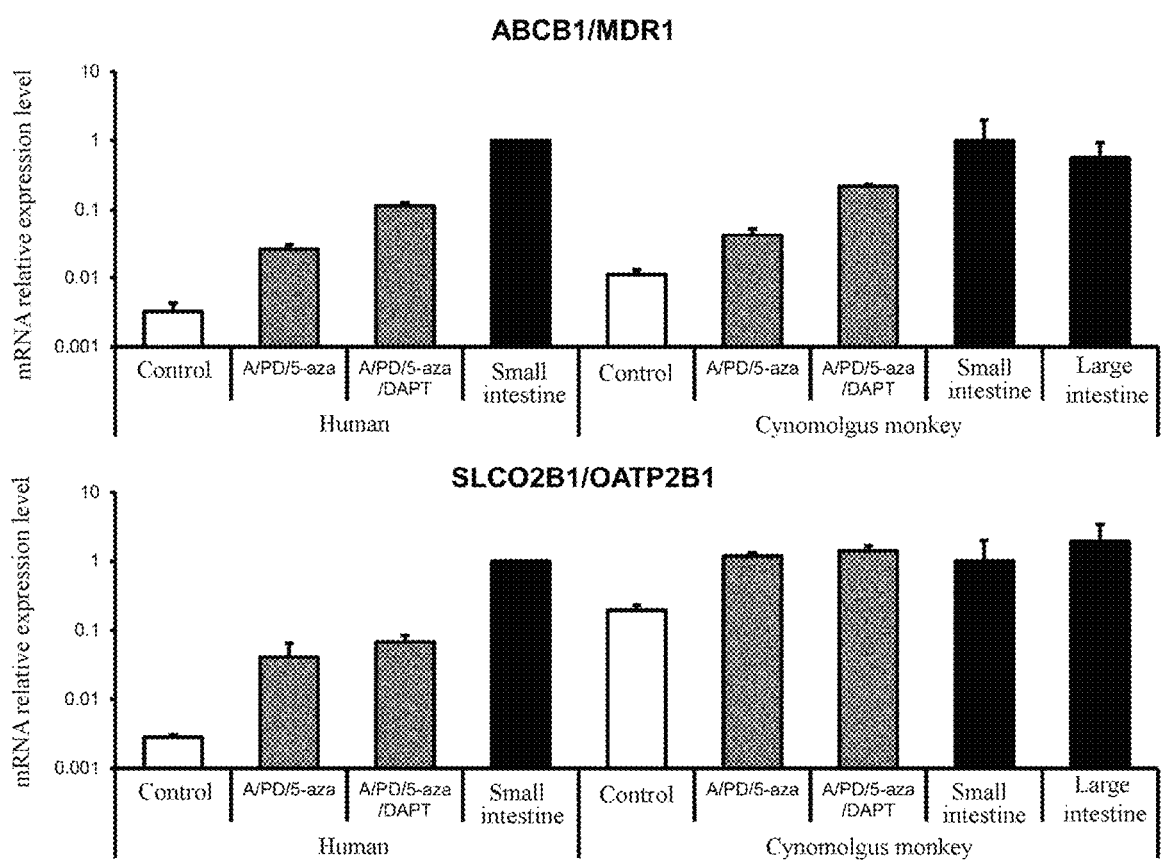
Figures 1, 2, 3:
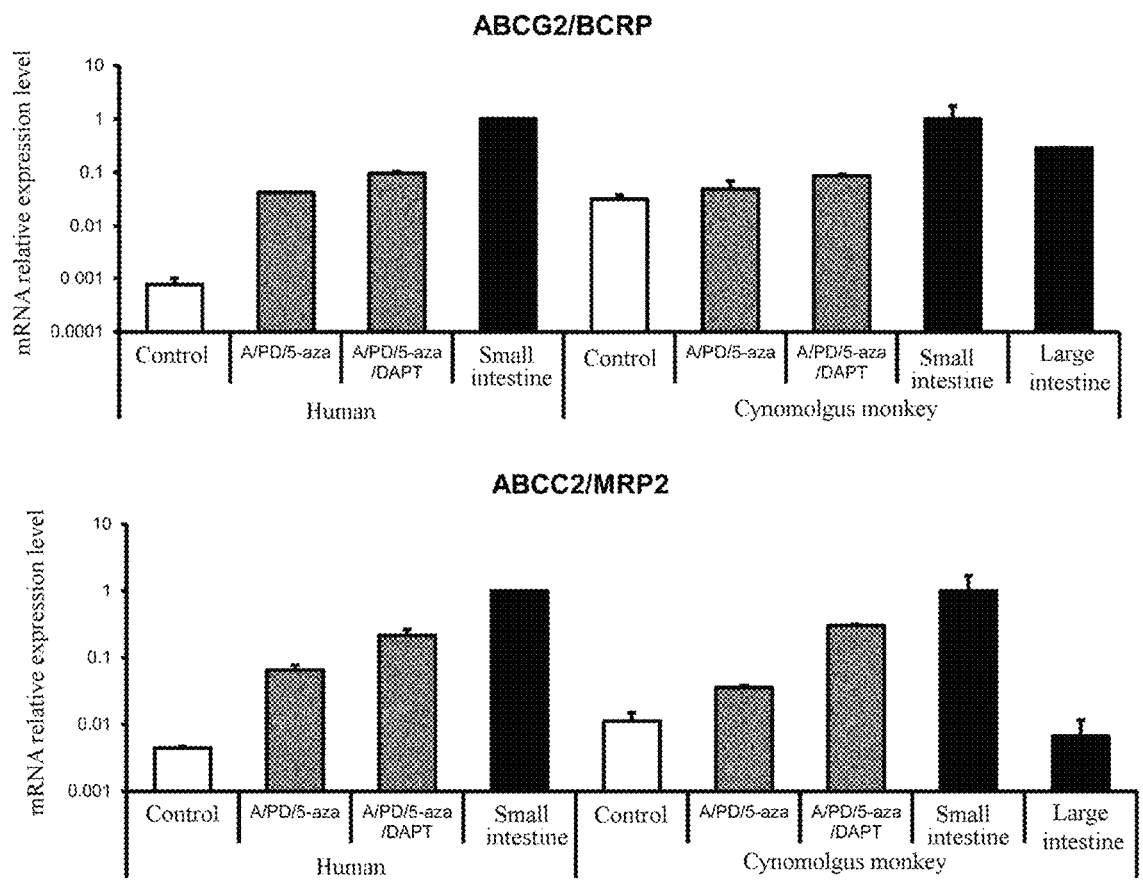
Figures 1, 2, 3, 4:
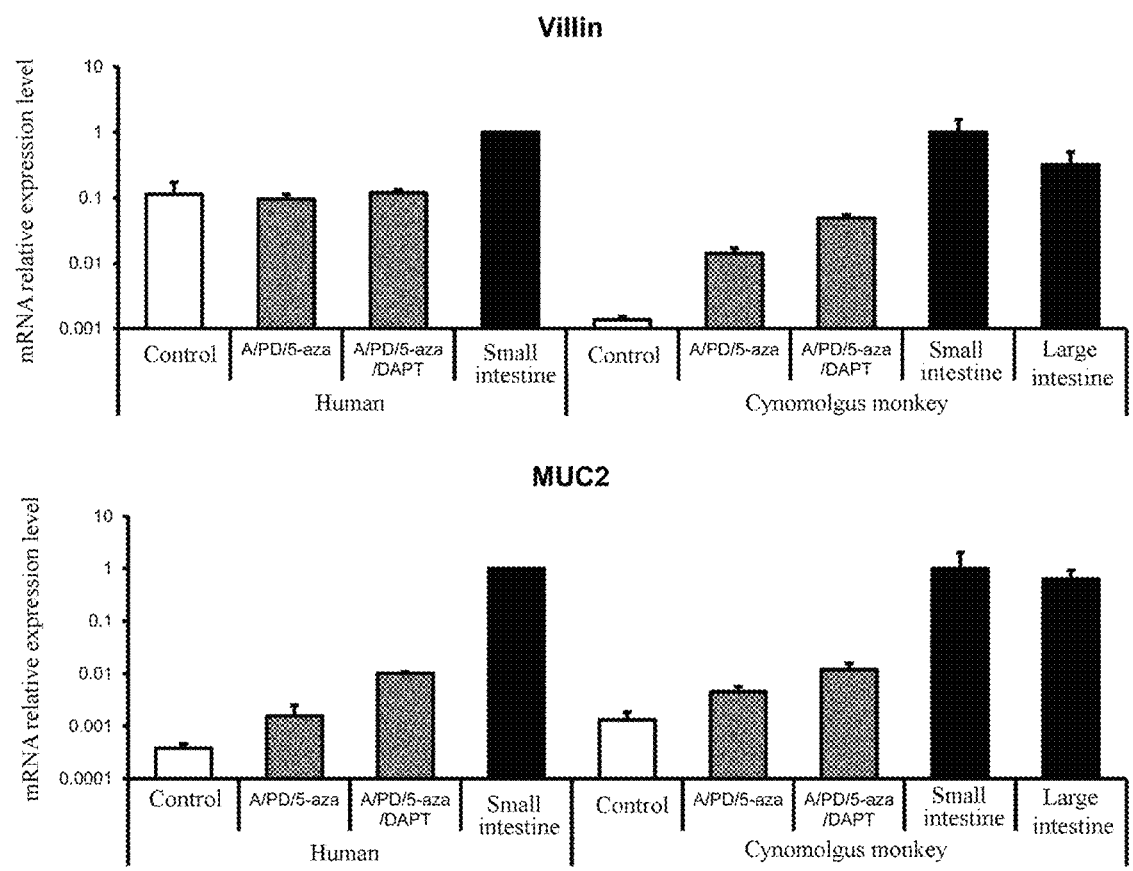
Figures 1, 10:
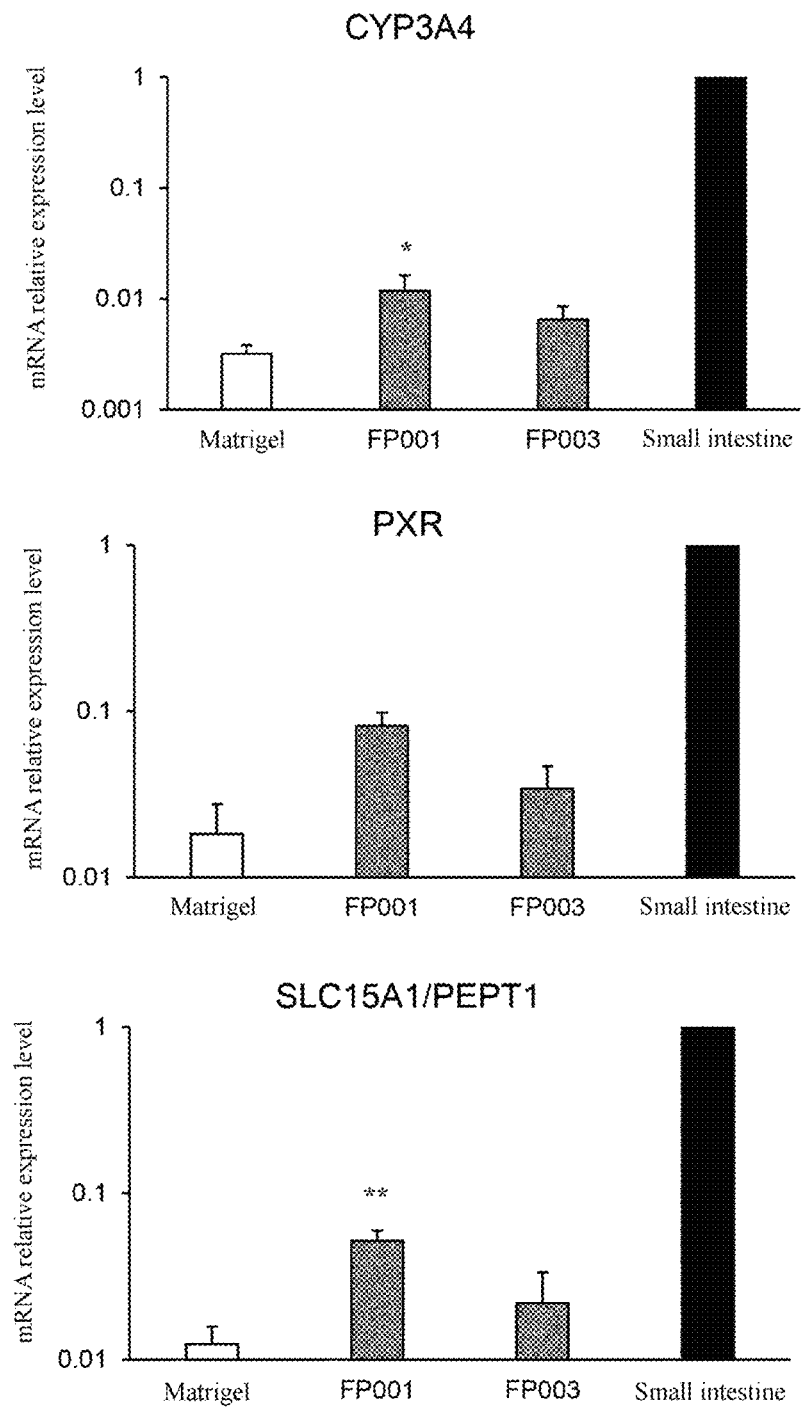
Figures 2, 10:
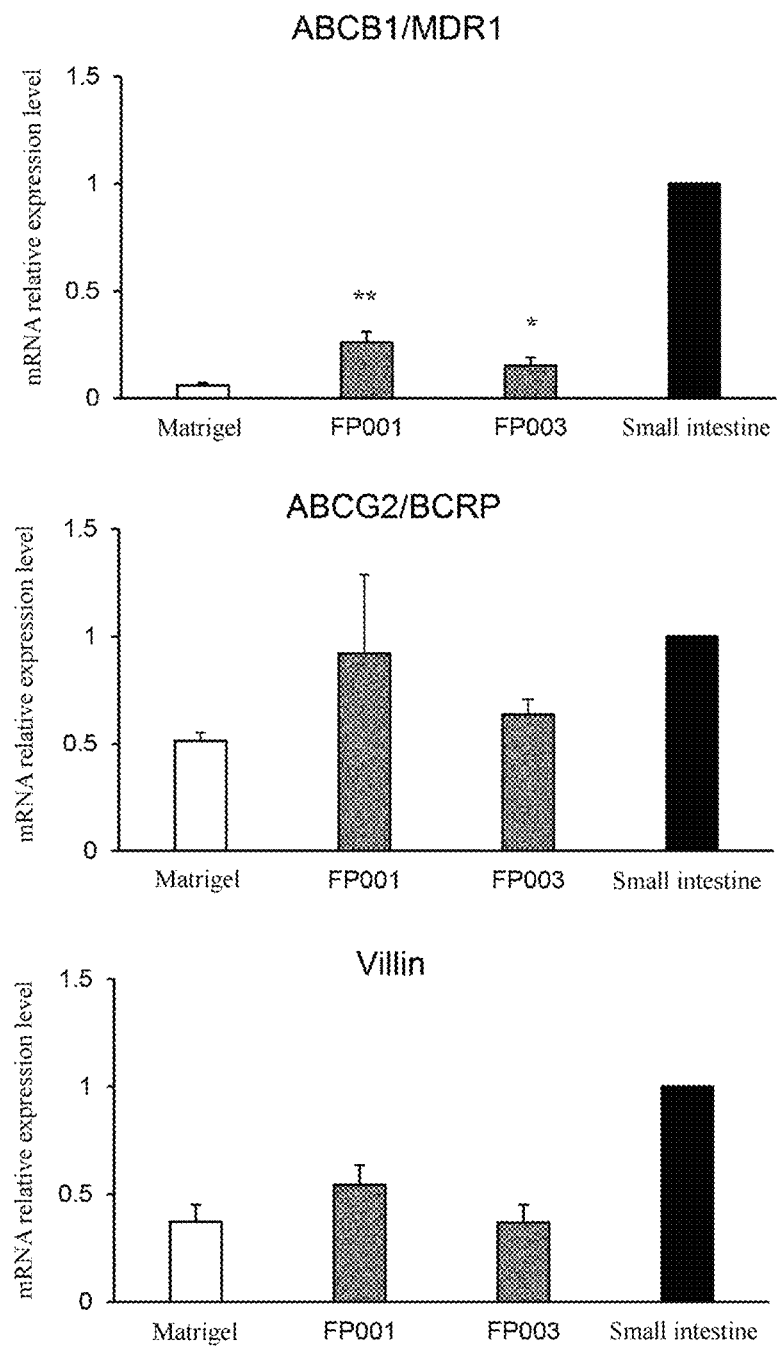
Figures 3, 10:
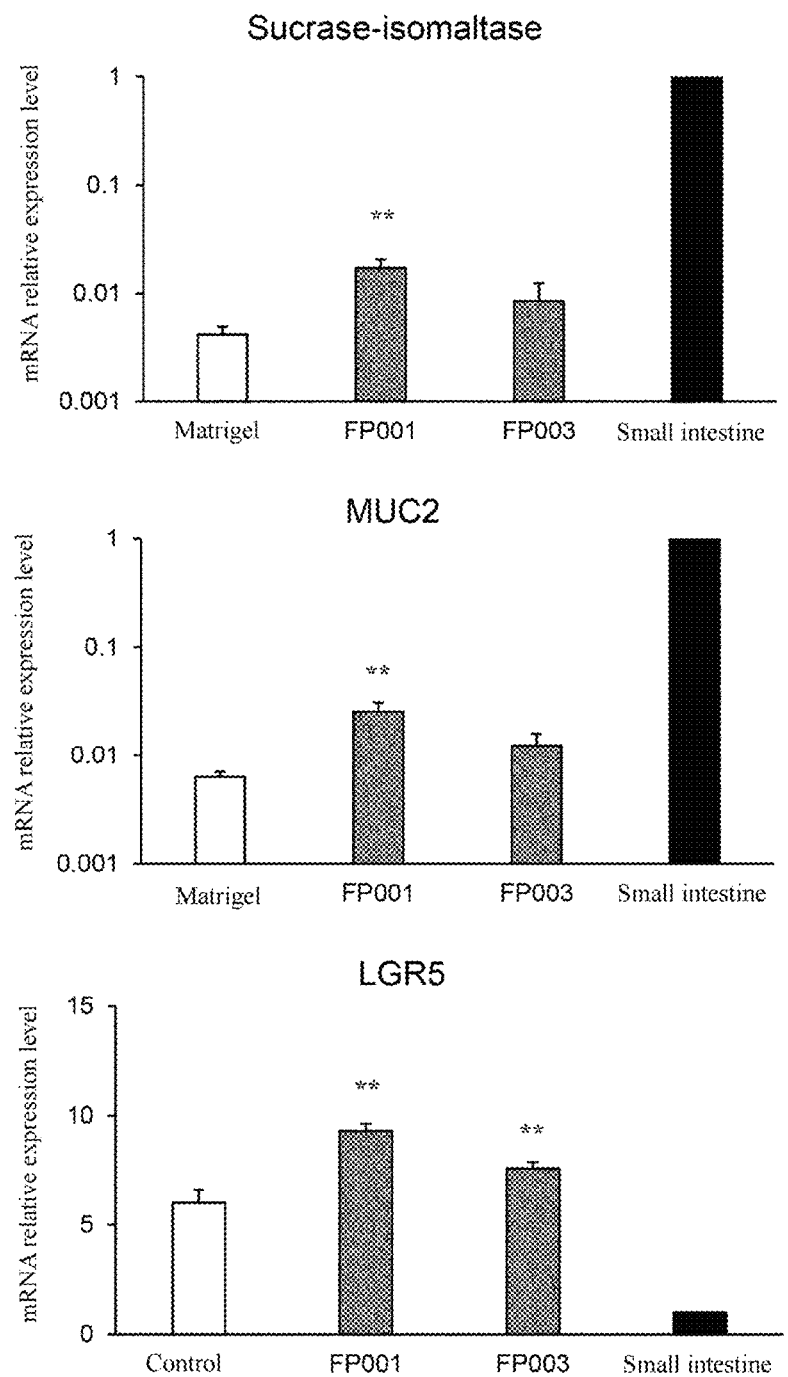
Figures 4, 10:
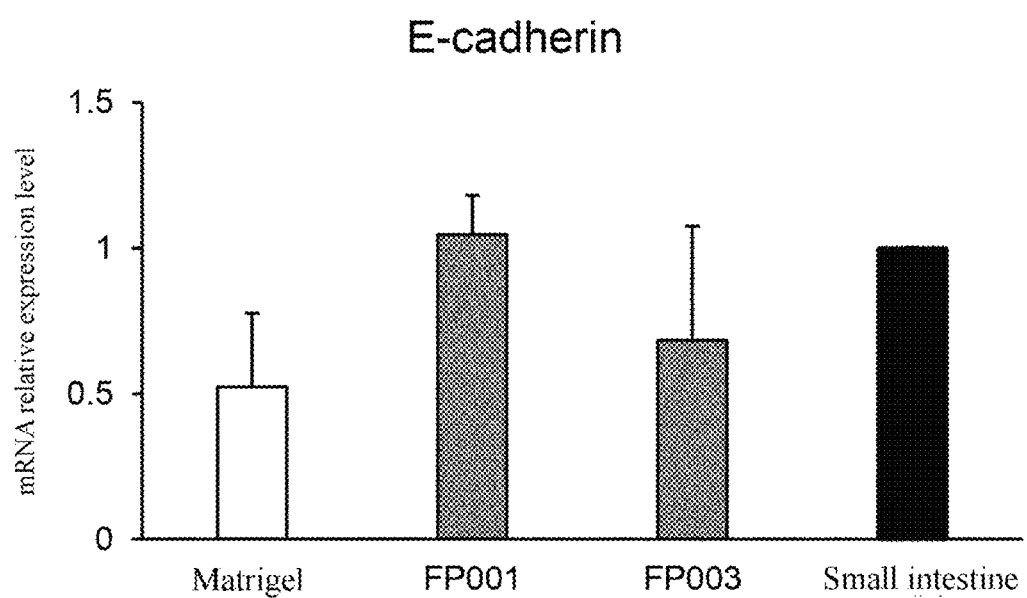

FIG. 10-1 Effects of polysaccharide polymers (FP001, FP003) on differentiation from human iPS cells into intestinal organoids. Data is shown as mean±S.D. (n=3). The value for the small intestine was used as a reference (small intestine=1). *P<0.05, **P<0.01 vs Matrigel FIG. 10-2 Continuation of FIG. 10.
FIG. 10-3 Continuation of FIG. 10.
FIG. 10-4 Continuation of FIG. 10.

Figure 11:
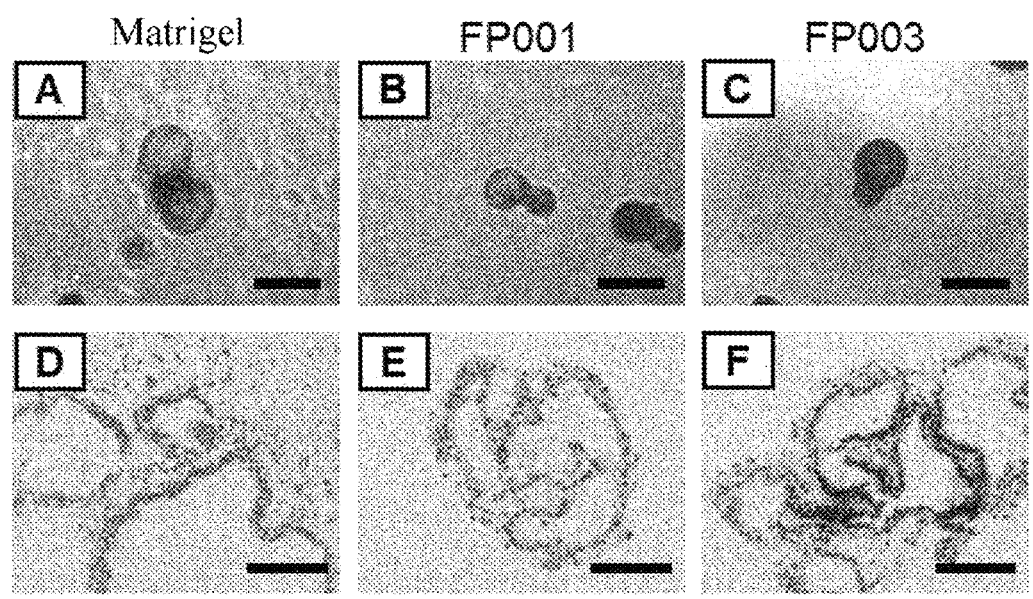

FIG. 11 Morphological observation of the human intestinal organoids obtained by differentiation induction using the polysaccharide polymers (FP001, FP003). (A)-(C): Bright field observation. Scale bar 500 µm. (D)-(F): HE staining Scale bar 100 µm.

Figure 12:
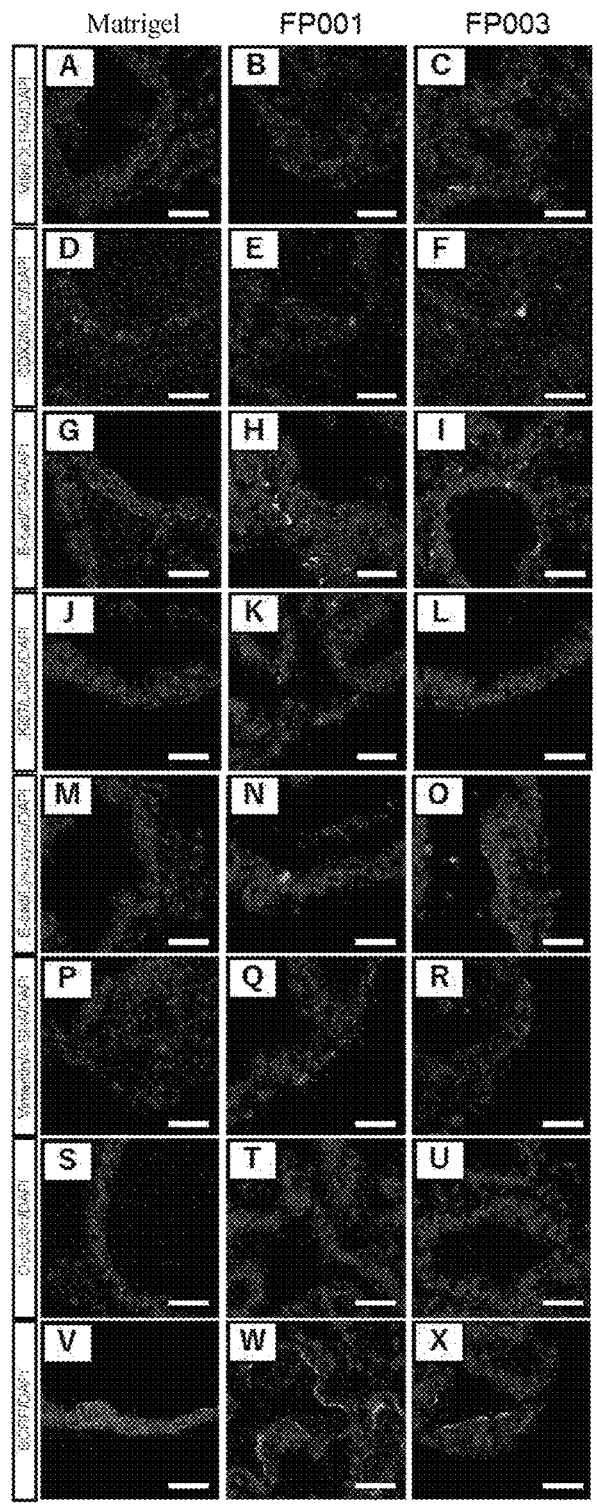

FIG. 12 Immunofluorescence staining of the human intestinal organoids obtained by differentiation induction using the polysaccharide polymers (FP001, FP003). (A)-(C): Villin/OLFM4. (D)-(F): CDX2 (cells of the intestinal lineage)/MUC2. (G)-(I): E-cad (epithelial cell adhesion factor)/CHGA (Chromogranin A). (J)-(L): Ki67 (proliferating cell marker)/LGR5 (stem cell marker). (M)-(O): E-cad/Lyso (Lysozyme). (P)-(R): Vim (Vimentin: fibroblast marker)/α-SMA (smooth muscle marker). (S)-(U): Occludin (tight junction). (V)-(X): ABCG2/BCRP (efflux transporter). DAPI: Nuclear staining. Scale bar 50 µm.

Figure 13:
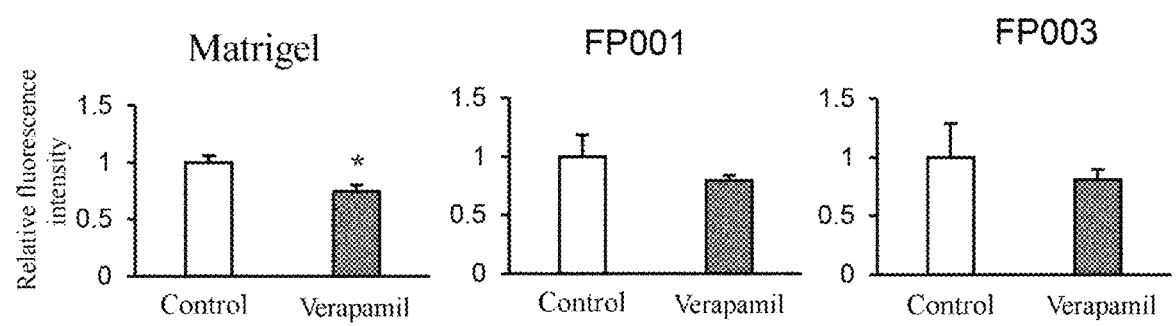

FIG. 13 Evaluation of the function of ABCB1/MDR1 using rhodamine 123 of the human intestinal organoids obtained by differentiation induction using the polysaccharide polymers (FP001, FP003). Verapamil (100 µmol/L) was used as an inhibitor of ABCB1/MDR1. Data is shown as mean±S.D. (n=3). The value for the control group (the inhibitor was not added) is used as a reference (control group=1). *P<0.05 vs control group.

Figure 14:
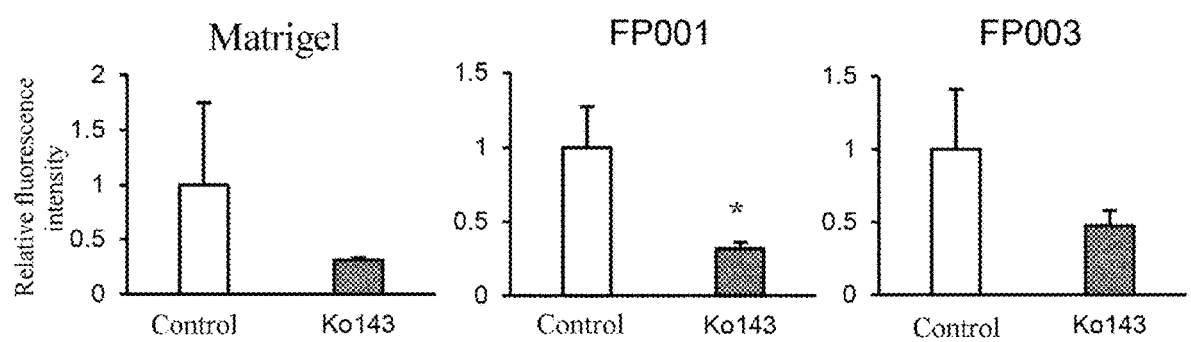

FIG. 14 Evaluation of the function of ABCG2/BCRP using Hoechst 33342 of the human intestinal organoids obtained by differentiation induction using the polysaccharide polymers (FP001, FP003). Ko143 (20 µmol/L) was used as an inhibitor of ABCG2/BCRP. Data is shown as mean±S.D. (n=3). The value for the control group (the inhibitor was not added) is used as a reference (control group=1). *P<0.05 vs control group.

Figure 15:
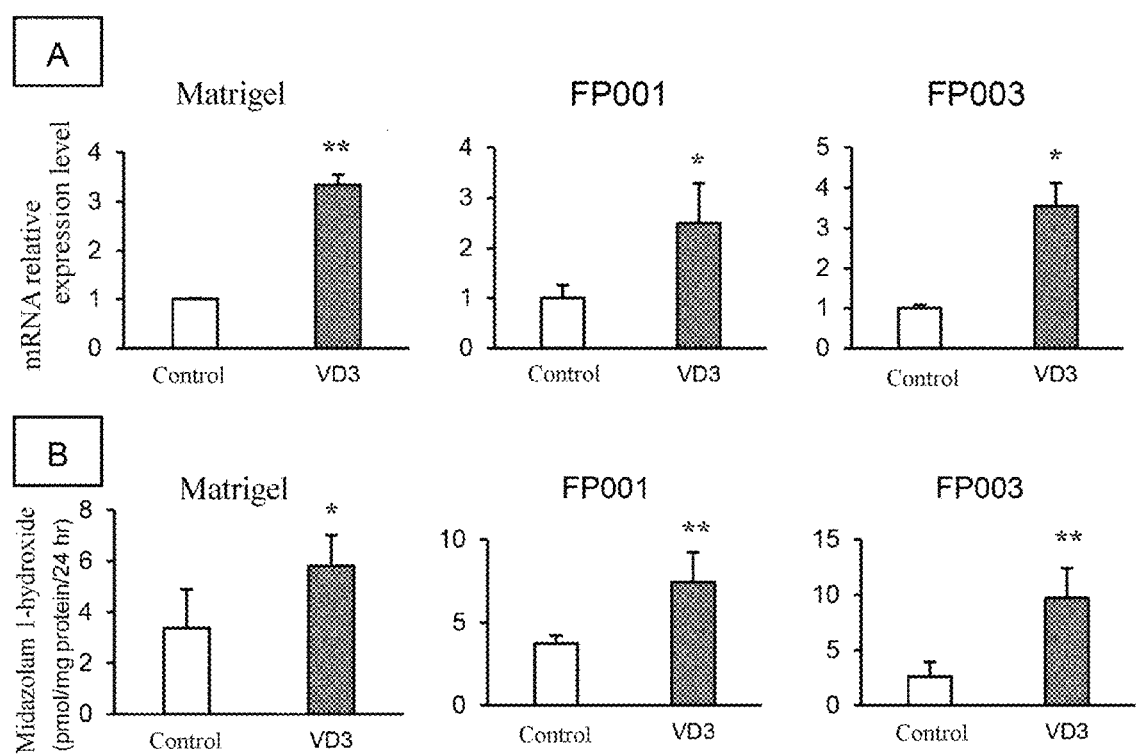

FIG. 15 CYP3A4 induction ability of the human intestinal organoids obtained by differentiation induction using the polysaccharide polymers (FP001, FP003). (A) Data is shown as mean±S.D. (n=3). Control; group to which no inducer was added. **P<0.01, *P<0.05 vs control group. The value for the control group is used as a reference (control group=1). (B) Data is shown as mean±S.D. (n=4). Control; group to which no inducer was added. **P<0.01, *P<0.05 vs control group.

Figure 16:
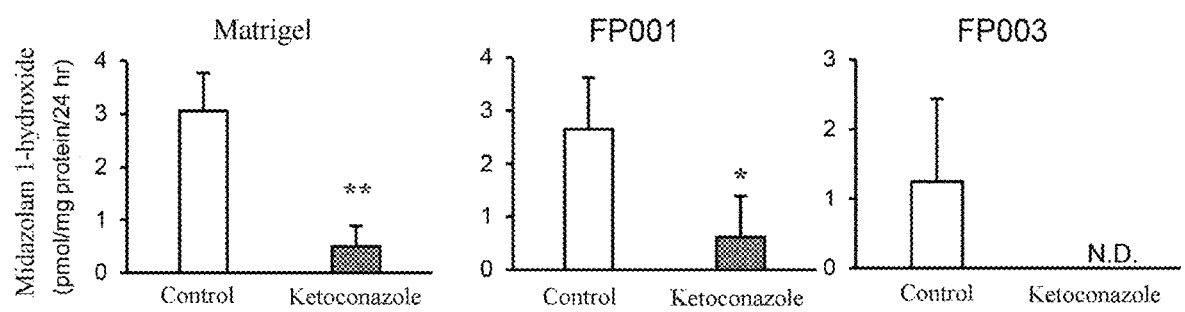

FIG. 16 CYP3A4 metabolic activity of the human intestinal organoids obtained by differentiation induction using the polysaccharide polymers. Data is shown as mean±S.D. (n=4). Control; group to which no ketoconazole was added. N.D.; not detected. **P<0.01, *P<0.05 vs control group.

DESCRIPTION OF EMBODIMENTS

1. Method for Preparing Intestinal Organoid

The present invention relates to a method for preparing an intestinal organoid from pluripotent stem cells (hereinafter also referred to as "the preparation method of the present invention"). According to the present invention, an intestinal organoid, which is three-dimensional tissue structures that exhibit characteristics similar to those of living intestinal tissue (mimic intestinal tissue), are obtained.

The "pluripotent stem cell" refers to a cell having both the potential for differentiating into all cells constituting the body (pluripotency), and the potential for producing daughter cells having the same differentiation potency via cell division (self-replication competence). The pluripotency can be evaluated by transplanting cells of an evaluation subject into a nude mouse, and testing the presence or absence of formation of teratoma containing each cell of the three germ layers (ectoderm, mesoderm, and endoderm).

Examples of the pluripotent stem cells include embryonic stem cells (ES cells), embryonic germ cells (EG cells), and induced pluripotent stem cells (iPS cells), but the cells are not limited thereto as long as they have both the pluripotency and the self-replication competence. ES cells or iPS cells are preferably used. More preferably, iPS cells are used. Preferably, pluripotent stem cells are cells of mammals (for example, primates such as humans, chimpanzees or cynomolgus monkey, and rodents such as mice or rats), and particularly preferably, pluripotent stem cells are human cells.

ES cells can be established by culturing, for example, a pre-implantation early embryo, an inner cell mass that constitutes the early embryo, a single blastomere, and the like (Manipulating the Mouse Embryo A Laboratory Manual, Second Edition, Cold Spring Harbor Laboratory Press (1994); Thomson, J A et al., Science, 282, 1145-1147 (1998)). As the early embryo, an early embryo prepared by nuclear-transplanting the nucleus of a somatic cell may be used (Wilmut et al. (Nature, 385, 810 (1997)), Cibelli et al. (Science, 280, 1256 (Nature, 394, 369 (1998)), Akira IRITANI et al. (Tanpakushitsu Kakusan Koso, 44, 892 (1999)), Baguisi et al. (Nature Biotechnology, 17, 456 (1999)), Wakayama et al. (Nature, 394, 369 (1998); Nature Genetics, 22, 127 (1999); Proc. Natl. Acad. Sci. USA, 96, 14984 (1999)), Rideout III et al. (Nature Genetics, 24, 109 (2000), Tachibana et al. Human Embryonic Stem Cells Derived by Somatic Cell Nuclear Transfer, Cell (2013) in press). As an early embryo, a parthenogenetic embryo may also be used: Kim et al. (Science, 315, 482-486 (2007)), Nakajima et al. (Stem Cells, 25, 983-985 (2007)), Kim et al. (Cell Stem Cell, 1, 346-352 (2007)), Revazova et al. (Cloning Stem Cells, 9, 432-449 (2007)), Revazova et al. (Cloning Stem Cells, 10, 11-24 (2008)). In addition to the above-mentioned papers, Stregkchenko N., et al. Reprod Biomed Online. 9: 623-629, 2004; Klimanskaya I., et al. Nature 444: 481-485, 2006; Chung Y, et al. Cell Stem Cell 2: 113-117, 2008; Zhang X., et al. Stem Cells 24: 2669-2676, 2006; Wassarman, P. M. et al. Methods in Enzymology, Vol. 365, 2003, etc. may also be referred to, as for the preparation of ES cells. Fused ES cells obtained by cell fusion of ES cells and somatic cells are also included in the embryonic stem cells used for the preparation method of the present invention.

Some ES cells are available from preservation institutes or commercially available. For example, human ES cells are available from the Institute for Frontier Medical Sciences, Kyoto University (for example, KhES-1, KhES-2, and KhES-3), WiCell Research Institute, ESI BIO, and the like.

EG cells can be established by culturing primordial germ cells in the presence of LIF, bFGF, SCF, and the like (Matsui et al., Cell, 70, 841-847 (1992), Shamblott et al., Proc. Natl. Acad. Sci. USA, 95 (23), 13726-13731 (1998), Turnpenny et al., Stem Cells, 21 (5), 598-609, (2003)).

The "induced pluripotent stem cell (iPS cell)" is a cell having pluripotency (multipotency) and proliferative ability, which is prepared by reprogramming a somatic cell by introduction of an initialization factor or the like. The induced pluripotent stem cell exhibits properties similar to those of an ES cell. The somatic cell used in the preparation of an iPS cell is not particularly limited, and may be a differentiated somatic cell or an undifferentiated stem cell. Also, its origin is not particularly limited, but somatic cells of mammals (for example, primates such as humans, chimpanzees or cynomolgus monkey, and rodents such as mice or rats), particularly preferably human somatic cells are used. iPS cells can be prepared by various methods reported so far. The application of iPS cell preparation methods which will be developed in the future is also necessarily contemplated.

By using iPS cells derived from patients suffering from bowel diseases (iPS cells prepared from somatic cells of patients), it is possible to prepare a disease-specific intestinal organoid. The iPS cells are prepared from somatic cells (for example, skin, blood, monocytes, and the like) collected from patients. Examples of the bowel diseases here include intractable inflammatory bowel diseases (Crohn's disease, ulcerative colitis), polyps, colorectal cancer, and drug-induced enteritis. A disease-specific intestinal organoid is useful as an intestinal pathologic model, and can be expected to be used in drug evaluation systems and to contribute to the elucidation of disease mechanisms (molecular mechanisms related to onset, pathogenesis, and progression).

The most fundamental technique of iPS cell preparation methods is to introduce four factors Oct3/4, Sox2, Klf4, and c-Myc, which are transcription factors, into cells using a virus (Takahashi K, Yamanaka S: Cell 126 (4), 663-676, 2006; Takahashi, K, et al.: Cell 131 (5), 861-72, 2007). The establishment of human iPS cells by introduction of four factors Oct4, Sox2, Lin28, and Nonog has been reported (Yu J, et al.: Science 318 (5858), 1917-1920, 2007). The establishment of iPS cells by introduction of the three factors other than c-Myc (Nakagawa M, et al.: Nat. Biotechnol. 26 (1), 101-106, 2008), two factors Oct3/4 and Klf4 (Kim J B, et al.: Nature 454 (7204), 646-650, 2008), or only Oct3/4 (Kim J B, et al.: Cell 136 (3), 411-419, 2009) has also been reported. Also, techniques of introducing a protein, which is an expression product of a gene, into cells (Zhou H, Wu S, Joo J Y, et al.: Cell Stem Cell 4, 381-384, 2009; Kim D, Kim C H, Moon J I, et al.: Cell Stem Cell 4, 472-476, 2009) have also been reported. On the other hand, it has been reported to be possible to improve the preparation efficiency and reduce the factors to be introduced, by using, for example, an inhibitor BIX-01294 against histone methyltransferase G9a, a histone deacetylase inhibitor valproic acid (VPA) or BayK8644 (Huangfu D, et al.: Nat. Biotechnol. 26 (7), 795-797, 2008; Huangfu D, et al.: Nat. Biotechnol. 26 (11), 1269-1275, 2008; Silva J, et al.: PLoS. Biol. 6 (10), e 253, 2008). Studies have also been advanced on gene transfer methods, and techniques utilizing not only retroviruses, but also lentiviruses (Yu J, et al.: Science 318 (5858), 1917-1920, 2007), adenoviruses (Stadtfeld M, et al.: Science 322 (5903), 945-949, 2008), plasmids (Okita K, et al.: Science 322 (5903), 949-953, 2008), transposon vectors (Woltjen K, Michael I P, Mohseni P, et al.: Nature 458, 766-770, 2009; Kaji K, Norrby K, Pac a A, et al.: Nature 458, 771-775, 2009; Yusa K, Rad R, Takeda J, et al.: Nat Methods 6, 363-369, 2009), or episomal vectors (Yu J, Hu K, Smuga-Otto K, Tian S, et al.: Science 324, 797-801, 2009) for gene transfer have been developed.

Cells in which transformation into iPS cells, i.e., initialization (reprogramming) has occurred can be selected by using, as an index, the expression of pluripotent stem cell markers (undifferentiation markers) such as Fbxo15, Nanog, Oct/4, Fgf-4, Esg-1, and Cript. The selected cells are collected as iPS cells.

iPS cells can also be provided, for example, from the National University Corporation Kyoto University or the Independent Administrative Institution RIKEN BioResource Center.

As used herein, the terms "differentiate" and "induce" mean acting to differentiate along a specific cell lineage. In the present invention, pluripotent stem cells are differentiated into an intestinal organoid. The preparation method of the present invention includes, roughly, the following four culturing steps (1) to (4):

(1) differentiating pluripotent stem cells into endoderm-like cells;
(2) differentiating the endoderm-like cells obtained in step (1) into intestinal stem cell-like cells;
(3) culturing the intestinal stem cell-like cells obtained in step (2) to form spheroids; and
(4) differentiating the spheroids formed in step (3) to form an intestinal organoid, the step including culture in the presence of a MEK1/2 inhibitor, a DNA methylation inhibitor, a TGF-β receptor inhibitor, and a γ-secretase inhibitor, in addition to an epidermal growth factor, a BMP inhibitor, and a Wnt signal activator. Hereinafter, details of the respective steps will be described.

<Step (1) Differentiation into Endoderm-Like Cells>

In this step, pluripotent stem cells are cultured and differentiated into endoderm-like cells. In other words, pluripotent stem cells are cultured under the conditions for inducing differentiation into endoderm-like cells. As long as pluripotent stem cell differentiate into endoderm-like cells, the culture conditions are not particularly limited. For example, iPS cells are cultured in a medium to which activin A has been added according to a conventional method. In this case, the concentration of activin A in the medium is, for example, 10 ng/mL to 200 ng/mL, preferably 20 ng/mL to 150 ng/mL. It is preferable to add serum or serum replacement (such as Knockout serum replacement (KSR)) to the medium from the viewpoint of cell growth rate, maintenance, and the like. The serum is not limited to fetal bovine serum, and human serum, sheep serum, etc. can also be used. The amount of the serum or serum replacement to be added is, for example, 0.1% (v/v) to 10% (v/v).

Inhibitors of the Wnt/β-catenin signaling pathway (hexachlorophene, quercetin, Wnt ligand Wnt3a, etc.) may be added to the medium to promote differentiation into endoderm-like cells.

Two-stage culture may be carried out as step (1). The culture at the first stage is carried out in a medium to which a relatively low concentration of serum (for example, 0.1% (v/v) to 1% (v/v)) has been added, and the subsequent culture at the second stage is carried out in a medium having a serum concentration higher than that of the medium used at the first stage (serum concentration is, for example, 1% (v/v) to 10% (v/v)). Adopting the two-stage culture is preferable in that growth of undifferentiated cells is suppressed by the culture at the first stage and that differentiated cells are proliferated by the subsequent second stage.

The period of step (1) (culture period) is, for example, 1 day to 10 days, preferably 2 days to 7 days. When adopting the two-stage culture as step (1), the first-stage culture period is set to, for example, 1 day to 7 days, preferably 2 days to 5 days, and the second-stage culture period is set to, for example, 1 day to 6 days, preferably 1 day to 4 days.

<Step (2) Differentiation into Intestinal Stem Cell-Like Cells>

In this step, the endoderm-like cells obtained in step (1) are cultured and differentiated into intestinal stem cell-like cells. In other words, endodermal-like cells are cultured under the conditions for inducing differentiation into intestinal stem cell-like cells. As long as the endoderm-like cells differentiate into intestinal stem cell-like cells, the culture conditions are not particularly limited. In a case where human cells are used as pluripotent stem cells for step (1), preferably, culture is carried out in the presence of FGF4 (fibroblast growth factor 4) and Wnt agonist (e.g., Wnt3a, BML-284, 2-Amino-4-(3,4-(methylenedioxy)benzylamino)-6-(3-methoxyphenyl)pyrimidine). Preferably, human FGF4 (e.g., human recombinant FGF4) is used. On the other hand, in a case where cells of cynomolgus monkey, macaca mulatta, chimpanzees and the like are used as pluripotent stem cells, preferably, culture is carried out in the presence of FGF2 (fibroblast growth factor 2) and GSK-3 inhibitor (e.g., CHIR99021, CHIR98014, BIO, SB415286, SB216763, TWS119, A1070722). For example, human FGF2 (e.g., human recombinant FGF2) is used.

Typically, the cell population obtained through step (1) or a part thereof is subjected to step (2) without sorting. On the other hand, step (2) may be carried out after sorting endoderm-like cells from the cell population obtained through step (1). Sorting of endoderm-like cells may be performed, for example, with a flow cytometer (cell sorter) with the cell surface marker being used as an index.

The phrase "in the presence of FGF4 and Wnt agonist" is synonymous with the condition that FGF4 and Wnt agonist have been added to the medium. Therefore, in order to carry out culture in the presence of FGF4 and Wnt agonist, a medium to which FGF4 and Wnt agonist have been added may be used. An example of the concentration of FGF4 to be added is 100 ng/mL to 5 µg/mL, preferably 300 ng/mL to 1 µg/mL. An example of the concentration of Wnt agonist (in the case of Wnt3a) to be added is 100 ng/mL to 5 µg/mL, preferably 300 ng/mL to 1 µg/mL.

Similarly, the phrase "in the presence of FGF2 and GSK-3 inhibitor" is synonymous with the condition that FGF2 and GSK-3 inhibitor have been added to the medium. Therefore, in order to carry out culture in the presence of FGF2 and GSK-3 inhibitor, a medium to which FGF2 and GSK-3 inhibitor have been added may be used. An example of the concentration of FGF2 to be added is 50 ng/mL to 2.5 µg/mL, preferably 150 ng/mL to 500 ng/mL. An example of the concentration of GS K-3 inhibitor (in the case of CHIR99021) to be added is 600 nmol/L to 60 nmol/L, preferably 1 µmol/L to 20 µmol/L.

With respect to the addition concentration when compounds different from the exemplified compounds, i.e., Wnt3a, CHIR99021, are used, those skilled in the art can set the concentrations according to the above concentration ranges in view of the differences (in particular, difference in activity) between the properties of the compounds to be used and the properties of the exemplified compounds. The appropriateness of the set concentration ranges can be confirmed by preliminary experiments according to Examples described later.

The period of step (2) (culture period) is, for example, 2 days to 10 days, preferably 3 days to 7 days. If the culture period is too short, the expected effects (rise in differentiation efficiency and promotion of acquisition of functions as intestinal stem cells) cannot be obtained sufficiently. On the other hand, if the culture period is too long, the differentiation efficiency is lowered.

Differentiation into intestinal stem cell-like cells can be determined or evaluated, for example, using the expression of an intestinal stem cell marker as an index. Examples of the intestinal stem cell marker include leucine-rich repeat containing G-protein-coupled receptor 5 (LGR5) and Ephrin B2 receptor (EphB2).

<Step (3): Formation of Spheroids>

In this step, the intestinal stem cell-like cells obtained in step (2) are cultured to form spheroids. Suspension culture is suitable for forming such spheroids. In suspension culture, a culture vessel provided with a low cell adhesive or non-cell adhesive culture surface (for example, a culture surface with low cell adhesiveness/non-cell adhesiveness by treatment/binding of a polymer material, a hydrogel, or the like) is used, and the cells are cultured in a state of being away from the culture surface (i.e., in a floating state). The culture vessel used for suspension culture is not particularly limited, and, for example, a dish, a flask, a multiwell plate, a tube, a tray, a culture bag or the like can be used. Preferably, a culture vessel in which a plurality of wells uniform in shape and size are formed in a low cell adhesive or non-cell adhesive culture surface (generally referred to as a pattern plate; specific examples thereof can include EZSPHERE (registered trademark) provided by AGC TECHNO GLASS Co., Ltd. and Elplasia provided by KURARAY CO., LTD.) is used to form a plurality of spheroids together. In this way, spheroids can be formed efficiently, and thus the intestinal organoid preparation efficiency is improved.

In suspension culture, the cells/cell mass may be either statically cultured or subjected to gyratory culture or shake culture, as long as the non-adherent state to the culture surface can be maintained. Preferably, the suspension culture herein is performed by static culture. Static culture has many advantages, for example, that no special device is needed; that it is expected to be less impacted or damaged to cells; and that the amount of the culture solution can be reduced.

Culture conditions are not particularly limited as long as spheroids can be formed. Typically, suspension culture is performed in the presence of an epidermal growth factor (EGF), a BMP inhibitor, and a Wnt signal activator, that is, using a medium to which these ingredients are added, in order to form spheroids while maintaining stem cell properties.

The effect of promoting cell proliferation can be expected by using the epidermal growth factor. Moreover, the use of the BMP inhibitor can be expected to provide the effects of suppressing differentiation of stem cells and maintaining stem cell properties. The Wnt signal activator can be expected to provide the effect of maintaining stem cell proliferation and stem cell properties.

For example, Noggin can be used as the BMP inhibitor. Further, for example, R-spondin-1 can be used as the Wnt signal activator.

An example of the concentration of the epidermal growth factor to be added is 10 ng/mL to 500 ng/mL, preferably 50 ng/mL to 200 ng/mL. An example of the concentration of the BMP inhibitor to be added (in the case of Noggin) is 10 ng/mL to 500 ng/mL, preferably 50 ng/mL to 200 ng/mL. Similarly, an example of the concentration of the Wnt signal activator to be added (in the case of R-spondin-1) is 10 ng/mL to 1000 ng/mL, preferably 50 ng/mL to 500 g/mL.

When a compound different from the exemplified compounds, i.e., Noggin and R-spondin-1, is used, the concentration thereof to be added can be set according to the above-described concentration range by those skilled in the art in consideration of the difference in characteristics (particularly, difference in activity) between the compound used and the exemplified compounds. Whether or not the set concentration range is appropriate can be confirmed by preliminary experiments according to the Examples which will be described later.

The period of step (3) (culture period) is, for example, 1 day to 10 days, preferably 2 days to 7 days. If the culture period is too short, no sufficiently large spheroid is formed. On the other hand, if the culture period is too long, spheroids larger than necessary will be formed so that the cells within the spheroids may cause necrosis. Preferably, spheroids having a diameter of about 100 μm to 200 μm are formed. For example, by using a pattern plate in which wells having a diameter of 400 to 500 μm and a depth of 100 to 200 μm are uniformly formed, spheroids of the size can be formed.

<Step (4): Formation of Intestinal Organoid>

In this step, the spheroids formed in step (3) are differentiated to form an intestinal organoid. For this purpose, culture is performed in the presence of a MEK1/2 inhibitor, a DNA methylation inhibitor, a TGF-β receptor inhibitor, and a γ-secretase inhibitor, in addition to an epidermal growth factor, a BMP inhibitor, and a Wnt signal activator. The feature of using the combination of the MEK1/2 inhibitor, the DNA methylation inhibitor, the TGF-β receptor inhibitor, and the γ-secretase inhibitor is particularly characteristic in the present invention, which contributes to improvement of the differentiation induction efficiency and promotion of maturation of intestinal organoid.

Among the factors used for the culture in this step, specific examples of the epidermal growth factor, the BMP inhibitor, and the Wnt signal activator and the concentrations thereof to be added are the same as those in step (3), and thus the description thereof is omitted.

Examples of the MEK1/2 inhibitors can include PD98059, PD184352, PD184161, PD0325901, U0126, MEK inhibitor I, MEK inhibitor II, MEK1/2 inhibitor II, and SL327. Similarly, examples of the DNA methylation inhibitor can include 5-aza-2'-deoxycytidine, 5-azacytidine, RG108, and zebralin. As the TGF-β receptor inhibitor, it is preferable to use one exhibiting the inhibitory activity against one or more of TGF-β receptors ALK4, ALK5, and ALK7. For example, A-83-01, SB431542, SB-505124, SB525334, D4476, ALK5 inhibitor, LY2157299, LY364947, GW788388, and RepSox satisfy the condition. Examples of the γ-secretase inhibitors include N-[(3,5-difluorophenyl)acetyl]-L-alanyl-2-phenyl-1,1-dimethyl-ethyl ester-glycine (DAPT), L-685,458, Compound E (CAS 209986-17-4), (R)-Flurbiprofen, BMS299897, JLK6, LY-411575, R04929097, MK-0752, SCP0004, SCP0025, gamma-Secretase Inhibitor XI, gamma-Secretase Inhibitor XVI, gamma-Secretase Inhibitor I, gamma-Secretase Inhibitor VII, Semagacestat (LY450139), gamma-Secretase Inhibitor III, Compound 34, BMS-708163, Compound W, YO-01027 (Dibenzazepine), and Avagacestat (BMS-708163).

An example of the concentration of the MEK1/2 inhibitor to be added (in the case of PD98059) is 4 μM to 100 μM, preferably 10 to 40 μM. Similarly, an example of the concentration of the DNA methylation inhibitor to be added (in the case of 5-aza-2'-deoxycytidine) is 1 μM to 25 μM, preferably 2.5 μM to 10 μM. An example of the concentration of the TGF-β receptor inhibitor to be added (in the case of A-83-01) is 0.1 μM to 2.5 μM, preferably 0.2 μM to 1 μM. An example of the concentration of the γ-secretase inhibitor to be added (in the case of DAPT) is 1 nM to 20 μM, preferably 0.1 μM to 10 μM.

When a compound different from the exemplified compounds, i.e., PD98059, 5-aza-2'-deoxycytidine, A-83-01, and DAPT, is used, the concentration thereof to be added can be set according to the above-described concentration range by those skilled in the art in consideration of the difference in characteristics (particularly, difference in activity) between the compound used and the exemplified compounds. Whether or not the set concentration range is appropriate can be confirmed by preliminary experiments according to the Examples which will be described later.

In order to form intestinal organoids from spheroids, the culture in step (4) is carried out in suspension. In the suspension culture herein, preferably, a liquid medium to which a material which is able to form a three-dimensional network structure in an aqueous solution is added is used, to culture the plurality of spheroids formed in step (3) together in suspension (i.e., in a state where the plurality of spheroids coexist in one culture vessel). That is, in a preferred embodiment, a part (however, two or more) or all of the spheroids formed in step (3) are subjected to suspension culture using a characteristic liquid medium.

By using a material which is able to form a three-dimensional network structure in an aqueous solution (hereinafter referred to as "viscous material"), spheroids are captured or trapped in the network structure, or the viscosity of the medium is increased so that the movement of the spheroids is restricted, thereby making it possible to prevent association and aggregation of the spheroids. Therefore, the plurality of spheroids can be cultured together in suspension, thereby enabling efficient formation of intestinal organoid.

As the viscous material, for example, a polymer gel or a polysaccharide can be used. Examples of the polymer gel include collagen, polymer hydrogel, and Matrigel™ (common Matrigel, growth factor-reduced (GFR) Matrigel with a reduced growth factor content, and the like). Examples of the polysaccharide include gellan gum, crystalline cellulose, nanocellulose, carboxycellulose, and carboxymethylcellulose. Two or more types of materials may be used in combination.

In a preferred embodiment, a polymer compound having an anionic functional group is used as the viscous material. Examples of the anionic functional group include a carboxy group, a sulfo group, a phosphate group, and salts thereof, and a carboxy group or a salt thereof is preferable. As the polymer compound used in the present invention, a polymer compound having one or two or more selected from the group of anionic functional groups can be used. Preferable specific examples of the polymer compound herein include, but not particularly limited to, a polysaccharide obtained by polymerizing 10 or more monosaccharides (for example, triose, tetrose, pentose, hexose, heptose, and the like). More preferable one is an acidic polysaccharide having an anionic functional group. The acidic polysaccharide referred to herein is not particularly limited as long as it has an anionic functional group in its structure, and examples thereof include polysaccharides having uronic acid (for example, glucuronic acid, iduronic acid, galacturonic acid, or mannuronic acid), polysaccharides having a sulfate group or phosphate group in a part of the structure, or polysaccharides having both the structures, which are not only naturally-occurring polysaccharides, but also polysaccharides produced by microorganisms, polysaccharides produced by genetic engineering, or polysaccharides artificially synthesized using enzymes. More specific examples thereof include those composed of one or two or more selected from the group consisting of hyaluronic acid, gellan gum, deacylated gellan gum, rhamsan gum, diutan gum, xanthan gum, carrageenan, xanthan gum, hexuronic acid, fucoidan, pectin, pectinic acid, pectinic acid, heparan sulfuric acid, heparin, heparitin sulfuric acid, kerato sulfuric acid, chondroitin sulfuric acid, dermatan sulfuric acid, and rhamnan sulfuric acid, and salts thereof. The polysaccharide is preferably hyaluronic acid, deacylated gellan gum, diutan gum, xanthan gum, carrageenan, or a salt thereof, and most preferably deacylated gellan gum in view of the fact that the object can be achieved by using a low concentration thereof. Examples of the salt referred to herein include salts of alkali metals such as lithium, sodium, and potassium, salts of alkaline earth metals such as calcium, barium, and magnesium, and salts of aluminum, zinc, copper, iron, ammonium, organic bases, and amino acids.

The weight average molecular weight of the polymer compound (polysaccharides and the like) is preferably 10,000 to 50,000,000, more preferably 100,000 to 20,000,000, still more preferably 1,000,000 to 10,000,000. For example, the molecular weight can be measured in pullulan conversion by gel permeation chromatography (GPC).

Furthermore, phosphorylated deacylated gellan gum can also be used. The phosphorylation can be performed by a known method.

In the present invention, a plurality (preferably two) of the polysaccharides described above may be used in combination. The type of combination of polysaccharides is not particularly limited as long as the combination can prevent association and aggregation of spheroids. Preferably, the combination includes at least deacylated gellan gum or a salt thereof. That is, a suitable combination of polysaccharides includes deacylated gellan gum or its salt, and polysaccharides other than deacylated gellan gum or its salts (e.g., xanthan gum, alginic acid, carrageenan, diutan gum, methylcellulose and locust bean gum, or their salts). Examples of specific combination of polysaccharides include, but are not limited to, deacylated gellan gum and rhamsan gum, deacylated gellan gum and diutan gum, deacylated gellan gum and xanthan gum, deacylated gellan gum and carrageenan, deacylated gellan gum and xanthan gum, deacylated gellan gum and locust bean gum, deacylated gellan gum and κ-carrageenan, deacylated gellan gum and sodium alginate, and deacylated gellan gum and methylcellulose.

More preferable specific examples of the viscous material used in the present invention include hyaluronic acid, deacylated gellan gum, diutan gum, carrageenan, and xanthan gum, and salts thereof, and a most preferable example thereof is deacylated gellan gum or a salt thereof. In the case of deacylated gellan gum, commercially available products such as "KELCOGEL (registered trademark of CP Kelco) CG-LA" manufactured by SANSHO Co., Ltd. and "Kelcogel (registered trademark of CP Kelco)" manufactured by San-Ei Gen F.F.I., Inc. can be used. In addition, "Kelcogel (registered trademark of CP Kelco) HT" manufactured by San-Ei Gen F.F.I., Inc. can be used as a native type gellan gum. Examples of particularly preferable viscous materials include polymer FP001 or polymer FP003 provided by Nissan Chemical Industries, Ltd. Polymer FP001 is an ingredient of the three-dimensional culture medium FCeM (registered trademark) series manufactured by Nissan Chemical Industries, Ltd., and polymer FP003 is an ingredient of FCeM (registered trademark) Advance Preparation Kit manufactured by the same company.

The amount of the viscous material to be used, that is, the amount thereof to be added to the medium is not particularly limited as long as the above-described effect can be exhibited. For example, the amount of the viscous material to be used is adjusted so that the viscosity of the medium ranges from 5 mPas·s to 2000 mPas·s. Too low a viscosity of the medium cannot provide the effect of preventing spheroid association and aggregation. On the other hand, too high a viscosity of the medium may affect the operability (handling) (for example, the recovery operation becomes complicated), and may also affect the supply of the medium ingredients to the cells. When the case of Matrigel is indicated as a specific example of the amount of the viscous material to be used, the amount of Matrigel to be used is preferably about 1% to 10% of the amount to be used in normal use (that is, use as a substrate for three-dimensional culture). Further, in the case of deacylated gellan gum, it is preferably added, in an amount of 0.001% to 1.0% (w/v), preferably 0.003% to 0.5% (w/v), more preferably 0.005% to 0.3% (w/v), still more preferably 0.01% to 0.05% (w/v), most preferably 0.01% to 0.03% (w/v), to the medium.

The culture vessel used for suspension culture is not particularly limited, and, for example, a dish, a flask, a multiwell plate, a tube, a tray, a culture bag, or the like can be used.

Note that the period (culture period) of step (4) is, for example, 12 days to 36 days.

Preferably, as step (4), the following steps (4-1) and (4-2) are performed in this order. In this embodiment, the combination of low molecular weight compounds characteristic of step (4) (i.e., the combination of the MEK1/2 inhibitor, the DNA methylation inhibitor, the TGF-β receptor inhibitor, and the γ-secretase inhibitor) is to be used in step (4-2).

<Step (4-1)>

This step can be positioned as a preparatory stage before promotion of aggressive differentiation induction by a combination of four types of low molecular weight compounds (MEK1/2 inhibitor, DNA methylation inhibitor, TGF-β receptor inhibitor, and γ-secretase inhibitor). By interposing this step, the growth of spheroids is promoted, which is advantageous for the construction of functional intestinal organoid. The culture in this step can be performed under the same conditions as those in step (3) (i.e., suspension culture in the presence of the epidermal growth factor, the BMP inhibitor, and the Wnt signal activator), but preferably the plurality of spheroids formed in step (3) are cultured together in suspension using a liquid culture medium to which a material (viscous material) which is able to form a three-dimensional network structure in an aqueous solution is added, thereby improving operability and efficiency.

The period of step (4-1) (culture period) is, for example, 3 days to 15 days, preferably 6 days to 12 days. If the culture period is too short, spheroids are small and likely to cause cell death. On the other hand, if the culture period is too long, no sufficient effects by virtue of the low molecular weight compounds can be obtained.

<Step (4-2)>

In this step, suspension culture is performed in the presence of the MEK1/2 inhibitor, the DNA methylation inhibitor, the TGF-β receptor inhibitor, and the γ-secretase inhibitor in addition to the epidermal growth factor, the BMP inhibitor, and the Wnt signal activator to promote aggressive differentiation induction and to form an intestinal organoid. Since the culture conditions are the same as those in the above step (4), the description thereof is omitted.

The period (culture period) of step (4-2) is, for example, 3 days to 21 days, preferably 9 days to 18 days. Too short a culture period cannot lead to sufficient function improvement. On the other hand, too long a culture period may cause cell death due to damage to spheroids.

Other culture conditions (culture temperature and the like) in each of the steps (step (1), step (2), step (3), step (4), step (4-1), step (4-2)) constituting the present invention may be conditions generally adopted in culture of animal cells. Specifically, the cells may be cultured in an environment of, for example, 37° C. and 5% CO2. In addition, as a basic medium, an Iscove's modified Dulbecco's medium (IMDM) (for example, GIBCO), a Ham's F12 medium (HamF 12) (SIGMA, Gibco, etc.), a Dulbecco's modified Eagle's medium (D-MEM) (Nacalai tesque, Sigma, Gibco, etc.), a Glasgow basic medium (for example, Gibco), a RPMI 1640 medium, and the like can be used. Two or more kinds of basic media may be used in combination. In step (3) and step (4)(or steps (4-1) and (4-2)) constituting step (3), a basic medium suitable for culturing epithelial cells (a mixed medium of D-MEM and Ham F12, D-MEM, etc.) is preferably used. Examples of components that can be added to the medium can include bovine serum albumin (BSA), antibiotics, 2-mercaptoethanol, PVA, nonessential amino acids (NEAA), insulin, transferrin, and selenium.

Subculture may be performed in the middle of step (1) and step (2) constituting the present invention. For example, when the cells become confluent or sub-confluent, a part of the cells are collected and transferred to another culture vessel, and the culture is continued. A cell dissociation solution or the like may be used for cell recovery. As the cell dissociation solution, for example, protease such as trypsin-EDTA, collagenase IV, and metalloprotease can be used alone or in an appropriate combination. Cell dissociation solutions with low cell toxicity are preferred. As such cell dissociation solutions, for example, commercially available products such as DISPASE (EIDIA Co., Ltd.), TrypLE (Invitrogen) or Accutase (MILLIPORE) are available. The recovered cells may be subjected to subculture after treatment with a cell strainer or the like, in order that the cells are in a dispersed (discrete) state. On the other hand, in each step constituting the present invention, the medium is exchanged as needed. For example, the medium may be exchanged once per 24 hours to 3 days.

When recovering cells associated with subculture or medium exchange, in order to suppress cell death, it is preferable to preliminarily treat the cells with a ROCK inhibitor (Rho-associated coiled-coil forming kinase/Rho-binding kinase) such as Y-27632.

According to the present invention described above, a functional intestinal organoid can be prepared. The "functional intestinal organoid" is an intestinal organoid having a pharmacokinetic function characteristic of the intestinal tracts, which is observed to have a functional tight junction, and has a metabolic (absorption, excretion) function. A functional intestinal organoid can be evaluated by expression of a tight junction marker, expression of various transporters (a peptide transporter, an efflux transporter, an organic anion transporter, and the like), expression/activity of a drug metabolizing enzyme, and the like. In addition, the presence or absence and degree of drug responsiveness are also useful as indexes for evaluating the functionality of intestinal organoid. An example of the tight junction marker is Occludin; an example of the peptide transporter is SLC15A1/PEPT1 (SLC (solute carrier) family member 15A1/peptide transporter 1); examples of the efflux transporter are ABCB1/MDR1 (ATP binding cassette transporter B1/multidrug resistant protein 1), ABCC2/MRP2 (ATP binding cassette transporter C2/multidrug resistance-related protein 2), and ABCG2/BCRP (ATP binding cassette transporter G2/breast cancer resistant protein); an example of the organic anion transporter is SLCO2B1/OATP2B1 (SLC (solute carrier) organic anion transporter 2B1); and examples of the drug metabolizing enzyme are CYP3A4 (cytochrome P450 3A4) and CYP3A8 (cytochrome P450 3A8). For the evaluation of drug responsiveness, for example, induction of expression of the drug metabolizing enzyme CYP3A (for example, CYP3A4 for humans and CYP3A8 for cynomolgus monkeys) via a rifampicin or vitamin D receptor can be used as an index.

Note that CDX2 (Caudal-type homeobox 2), Chromogranin A, E-cad (E-cadherin; epithelial cadherin), LGR5 (G protein-coupled receptor including a leucine-rich repeat), Lysozyme, MUC2 (mucin 2 glycoprotein), OLFM4 (Olfactomedin 4), Villin, Vim (Vimentin), and the like are also useful for evaluating the structure or functionality of intestinal organoid.

2. Use of Intestinal Organoid

A second aspect of the present invention relates to use of the intestinal organoid prepared by the preparation method of the present invention. Various assays are provided as the first use. The intestinal organoid of the present invention can be used for model systems of the intestinal tract, particularly the small intestine, and are useful for evaluating pharmacokinetics (absorption, metabolism, etc.) and toxicity in the intestinal tract, particularly the small intestine. In other words, the intestinal epithelial cell-like cells of the present invention are intended to be used for evaluation of in vivo drug disposition of compounds and evaluation of their toxicity.

Specifically, the intestinal organoid of the present invention can be used to test the metabolism, absorption, membrane permeability, drug interaction, drug metabolizing enzyme induction, drug transporter induction, toxicity, and the like of the test substance. That is, the present invention provides a method for evaluating the metabolism, absorption, membrane permeability, drug interaction, drug metabolizing enzyme induction, drug transporter induction, toxicity, and the like of the test substance as one of the uses of intestinal organoid. In the method, there are carried out step (I) of bringing the test substance into contact with the intestinal organoid obtained by the preparation method according to the present invention; and step (II) of measuring/evaluating the metabolism, absorption, membrane permeability, drug interaction, drug metabolizing enzyme induction, drug transporter induction, or toxicity of the test substance.

The "contact" in step (I) is typically carried out by adding the test substance to the medium. The timing of adding the test substance is not particularly limited. Therefore, either the procedure of starting culture in a medium not containing the test substance and then adding the test substance at a certain time point or the procedure of starting culture in a medium containing the test substance in advance may be used.

As the test substance, organic or inorganic compounds having various molecular sizes can be used. Examples of the organic compounds include nucleic acids, peptides, proteins, lipids (simple lipids, complex lipids (phosphoglycerides, sphingolipids, glycosyl glycerides, cerebrosides, etc.)), prostaglandins, isoprenoids, terpenes, steroids, polyphenols, catechins, and vitamins (B1, B2, B3, B5, B6, B7, B9, B12, C, A, D, E, etc.). Existing components or candidate components such as drugs, nutritional foods, food additives, agricultural chemicals, cosmetic products (cosmetics), and the like are also preferable test substances. A plant extract, a cell extract, a culture supernatant, and the like may be used as the test substance. By simultaneously adding two or more kinds of test substances, interactions, synergistic actions, and the like between the test substances may be examined. The test substance may be derived from natural products or obtained by synthesis. In the latter case, for example, an efficient assay system can be constructed by using a combinatorial synthesis technique.

The period during which the test substance is brought into contact can be arbitrarily set. The contact period is, for example, 10 minutes to 3 days, preferably 1 hour to 1 day. Contact may be divided into a plurality of times.

After step (I), the metabolism, absorption, membrane permeability, drug interaction, drug metabolizing enzyme induction, drug transporter induction, or toxicity of the test substance is measured/evaluated (step (II)). Immediately after step (I), that is, after contact with the test substance, the metabolism or the like may be measured/evaluated without a substantial time interval, or the metabolism or the like may be measured/evaluated after the passage of a certain time (for example, 10 minutes to 5 hours). The metabolism can be measured, for example, by detecting a metabolite. In this case, the expected metabolite is usually measured qualitatively or quantitatively using the culture solution after step (I) as a sample. The measurement method may be selected appropriately depending on the metabolite. For example, mass spectrometry, liquid chromatography, immunological techniques (e.g., fluorescence immunoassay (FIA method), enzyme immunoassay (EIA method)) and the like can be employed.

Typically, when a metabolite of the test substance is detected, it is determined or evaluated that "the test substance has been metabolized". Also, the metabolic expenditure of the test substance can be evaluated according to the amount of the metabolite. The metabolic efficiency of the test substance may be calculated based on the detection result of the metabolite and the amount of the test substance used (typically, the amount thereof added to the medium).

It is also possible to measure the metabolism of the test substance using the expression of the drug metabolizing enzyme (cytochrome P450 (especially, CYP3A4 for humans, CYP3A8 for cynomolgus monkeys), uridine diphosphate-glucuronyltransferase (especially, UGT1A8, UGT1A10), sulfotransferase (especially, SULT1A3), and the like in an intestinal organoid as indexes. The expression of the drug metabolizing enzyme can be evaluated at the mRNA level or protein level. For example, when an increase in mRNA level of the drug metabolizing enzyme is observed, it can be determined that "the expression level at the gene level has increased". Similarly, when an increase in activity of the drug-metabolizing enzyme is observed, it can be determined that "the test substance has been metabolized". As in the case of determining a metabolite as an index, quantitative determination/evaluation may be performed based on the expression level of the drug metabolizing enzyme.

In order to evaluate the absorption of the test substance, for example, the amount of the test substance remaining in the culture solution is measured. Usually, the test substance is quantified using the culture solution after step (I) as a sample. An appropriate measurement method may be selected according to the test substance. For example, mass spectrometry, liquid chromatography, immunological techniques (e.g., fluorescence immunoassay (FIA method), enzyme immunoassay (EIA method)) and the like can be employed. Typically, when a decrease in content of the test substance in the culture solution is observed, it is determined/evaluated that "the test substance has been absorbed". Further, the amount of the test substance absorbed or the absorption efficiency can be determined/evaluated depending on the degree of decrease. Incidentally, the absorption can also be evaluated by measuring the amount of the test substance taken up into the cells.

The measurement/evaluation of metabolism and the measurement/evaluation of absorption may be performed simultaneously or in parallel.

As a second use of the intestinal organoid obtained by the preparation method of the present invention, a transplantation material including the intestinal organoid is provided. The transplantation material of the present invention is applicable to the treatment of various bowel diseases (for example, intractable inflammatory bowel diseases). In particular, the transplantation material is expected to be used as a material for regeneration/reconstruction of damaged (including dysfunctional) intestinal tissue. That is, the contribution to regenerative medicine can be expected. The transplantation material of the present invention can be utilized as the transplantation material as it is or after treatment such as embedding into Matrigel or collagen gel. In addition, utilization forms such as screening of therapeutic drug candidate compounds as various bowel disease pathological models and studies for elucidation of pathological mechanisms are also envisaged. In the transplantation material of the present invention, dimethylsulfoxide (DMSO) and serum albumin may be contained for the purpose of cell protection, antibiotics may be contained for the purpose of preventing bacterial contamination, and various ingredients (vitamins, cytokines, growth factors, steroids, and the like) may be contained for the purpose of cell activation, proliferation, or differentiation induction. In addition, other pharmaceutically acceptable ingredients (e.g., carriers, excipients, disintegrants, buffers, emulsifiers, suspensions, soothing agents, stabilizers, preservatives, antiseptics, physiological saline, and the like) may be contained in the transplantation material of the present invention.

The transplantation material of the present invention can also be used to construct an in vivo experimental system. For example, the transplantation material including an intestinal organoid prepared using human pluripotent stem cells can be transplanted into experimental animals such as mice, rats, guinea pigs, hamsters, pigs, cynomolgus monkeys, rhesus monkeys, chimpanzees, and the like to prepare humanized animals (human intestinal models). Such humanized animals are particularly useful for experiments such as pharmacokinetics and toxicity tests, and are expected to contribute to studies on the effects of first-pass effects on oral drugs and drug-induced enteritis.

An intestinal organoid prepared using iPS cells derived from patients with bowel diseases can be used as a model for intestinal pathology in drug evaluation systems, and also used in various experiments in studies to elucidate the mechanisms of the onset, pathogenesis and/or progression of bowel diseases.

EXAMPLES

<Preparation of iPS Cell-Derived Intestinal Organoids>

The following studies were conducted with the aim of creating a novel method for preparing a functional intestinal organoid.

1. Method
(1) Cells

Human iPS cells (iPS-51: Windy) were prepared by introducing octamer binding protein 3/4 (OCT3/4), sex determining region Y-box 2 (SOX2), kruppel-like factor 4 (KLF4), and v-myc myelocytomatosis viral oncogene homolog (avian) (c-MYC) into human fetal lung fibroblasts MRC-5 using a pantropic retrovirus vector and then cloning human ES cell-like colonies, and were provided by Dr. Akihiro Umezawa, National Center for Child Health and Development. Cynomolgus monkey iPS cells were prepared by introducing episomal vectors pCXLE-hOCT3/4-shp53-F, pCXLE-hSK, and pCXLE-hUL into fibroblasts cultured from cynomolgus monkey skin tissue by the electroporation method and then cloning cynomolgus monkey ES cell-like colonies, and established by the present inventors. Mouse embryonic fibroblasts (MEFs) were used as feeder cells.

(2) Medium

A Dulbecco's modified eagle medium (DMEM) containing 10% fetal bovine serum (FBS), 2 mmol/L L-glutamine (L-Glu), 1% non-essential amino acid (NEAA), 100 units/mL penicillin G, and 100 µg/mL streptomycin was used for culture of MEF. As an MEF stripping solution, used was 0.05% trypsin-ethylenediaminetetraacetic acid (EDTA). Cell Banker 1 was used as an MEF preservation solution. DMEM Ham's F-12 (DMEM/F12) containing 20% knockout serum replacement (KSR), 0.8% NEAA, 2 mmol/L L-Glu, 0.1 mmol/L 2-mercaptoethanol (2-MeE), and 5 ng/mL fibroblast proliferation factor (FGF) 2 was used for maintenance culture of the human iPS cells. For maintenance culture of the cynomolgus monkey iPS cells, DMEM/F12 containing 20% KSR, 1.0% NEAA, 2 mmol/L L-Glu, 100 units/mL penicillin G, 100 µg/mL streptomycin, 0.1 mmol/L 2-MeE, and 5 ng/mL FGF2 was used. Dulbecco's phosphate buffered saline (PBS) containing 1 mg/mL collagenase IV, 0.25% trypsin, 20% KSR, and 1 mmol/L calcium chloride was used as the stripping solution for the human and cynomolgus monkey iPS cells. As a preservation solution for the human and cynomolgus monkey iPS cells, a cryopreservation solution for primate ES/iPS cells was used.

(3) Culture of Human and Cynomolgus Monkey iPS Cells

Human iPS cells were seeded on MEF ($6\times10^5$ cells/100 mm dish) treated with mitomycin C, and cynomolgus monkey iPS cells were seeded on MEF ($1\times10^6$ cells/100 mm dish) treated with mitomycin C. The cells were cultured under the 5% $CO_2$/95% air condition at 37° C. in a $CO_2$ incubator. The human and cynomolgus monkey iPS cells were subcultured at a split ratio of 1:2 to 1:3 after 3 to 5 days of culture. For the human and cynomolgus monkey iPS cells, the medium was exchanged 48 hours after thawing and thereafter daily.

(4) Differentiation of Human and Cynomolgus Monkey iPS Cells into Intestinal Organoids The human and cynomolgus monkey iPS cells were seeded on a culture dish coated with Matrigel (with growth factors removed) diluted 30-fold in a culture medium for human and cynomolgus monkey iPS cells at the time of subculture, and cultured in a StemSure (registered trademark) hPSC medium containing 35 ng/mL FGF2, and the differentiation thereof into intestinal organoids started in a state in which the proportion of undifferentiated colonies arrived at about 80%. The iPS cells were cultured in a Roswell Park Memorial Institute (RPMI) medium containing 100 ng/mL activin A, 100 units/mL penicillin G, 100 µg/mL streptomycin, and 2 mmol/L L-Glu for 1 day, an RPMI medium containing 0.2% FBS, 100 ng/mL activin A, 100 units/mL penicillin G, 100 µg/mL streptomycin, and 2 mmol/L L-Glu for 1 day, and an RPMI medium containing 2% FBS, 100 ng/mL activin A, 100 units/mL penicillin G, 100 µg/mL streptomycin, and 2 mmol/L L-Glu for 1 day to be differentiated into the endoderm. Subsequently, the human iPS cells were differentiated into intestinal stem cells by culturing the iPS cells in an RPMI+glutamax medium containing 2% FBS, 500 ng/mL FGF4, 500 ng/mL Wnt3a, 100 units/mL penicillin G, and 100 µg/mL streptomycin for 4 days. The cynomolgus monkey iPS cells were differentiated into intestinal stem cells by culturing the iPS cells in an RPMI+glutamax medium containing 2% FBS, 250 ng/mL FGF2, 6 µmol/L CHIR99021, 100 units/mL penicillin G, and 100 µg/mL streptomycin for 4 days. After treatment with FGF4 and Wnt3a for the human iPS cells and after treatment with FGF4 and CHIR99021 for the cynomolgus monkey iPS cells, Y-27632 (Rho-binding kinase inhibitor) was added so as to attain 10 µmol/L, and cells treated under the 5% $CO_2$/95% air condition for 60 minutes at 37° C. in a $CO_2$ incubator were stripped with 0.05% trypsin-EDTA. The cell mass was crushed with a 40-µm nylon mesh cell strainer, and $7.0\times10^6$ cells were seeded on 100-mm EZSPHERE (registered trademark). Then, the cells were cultured in Advanced-DMEM/F12 containing 2 mmol/L L-Glu, 2% B27 supplement, 1% N2 supplement, 100 units/mL penicillin G, 100 µg/mL streptomycin, 100 ng/mL epidermal growth factor (EGF), 100 ng/mL Noggin, 200 ng/mL R-spondin-1, and 10 µmol/L Y-27632 for 3 days, and then cultured in suspension on an ultra-low adhesion 6-well plate in Advanced-DMEM/F12 containing 2 mmol/L L-Glu, 2% B27 supplement, 1% N2 supplement, 100 units/mL penicillin G, 100 µg/mL streptomycin, 100 ng/mL EGF, 100 ng/mL Noggin, 200 ng/mL R-spondin-1, and 3% Matrigel with growth factors removed for 24 days to be differentiated into intestinal organoids. The treatment of the drug-metabolizing enzyme with the inducer was performed by adding rifampicin or 1α,25-dihydroxyvitamin $D_3$ (VD3) to attain 40 µmol/L or 1 µmol/L, respectively, to Advanced-DMEM/F12 containing 2 mmol/L L-Glu, 2% B27 supplement, 1% N2 supplement, 100 units/mL penicillin G, 100 µg/mL streptomycin, 100 ng/mL EGF, 100 ng/mL Noggin, 200 ng/mL R-spondin-1, and 3% Matrigel with growth factors removed, followed by culture for 72 hours before recovery. Furthermore, from Days 19 to 34 from the start of differentiation, 5 µmol/L N-[(3,5-difluorophenyl)acetyl]-L-alanyl-2-phenyl-1,1-dimethylethyl ester-glycine (DAPT) was added, in addition to PD98059 (20 µmol/L), 5-aza-2'-deoxycytidine (5 µmol/L), and A-83-01 (0.5 µmol/L) as our previously found low molecular weight compounds. Then, the effects on differentiation into intestinal organoids were examined. The outline of the above culture method (differentiation protocol) is shown in FIG. 9.

(5) Extraction of Total Ribonucleic Acid (RNA)

Total RNA was extracted according to the attached manual of Agencourt RNAdvence Tissue after end of differentiation induction of the human and cynomolgus monkey iPS cells.

(6) Reverse Transcription Reaction

Complementary DNA (cDNA) was synthesized using ReverTra Ace qPCR RT Master Mix according to the attached manual.

(7) Real-Time RT-PCR method

For Real-Time RT-PCR, KAPA SYBR Fast qPCR Kit was used, and the cDNA was used as a template. The reaction was performed according to the attached manual. The results were corrected using glyceraldehyde-3-phosphate dehydrogenase (GAPDH) as an endogenous control.

(8) Hematoxylin-Eosin (HE) Staining and Alcian Blue Staining

After completion of differentiation induction, the intestinal organoid was fixed with 4% paraformaldehyde, and frozen and embedded with an OCT compound. A frozen section having a thickness of 10 μm was prepared and then attached to a slide glass. HE staining was performed using Mayer's hematoxylin and eosin alcohol. In Alcian blue staining, Alcian blue at pH 2.5 was used for staining, and Nuclea Fast Red was used as a nuclear staining reagent.

(9) Immunofluorescence Staining

After completion of differentiation induction, the intestinal organoid was fixed with 4% paraformaldehyde, and frozen and embedded with an OCT compound. A frozen section having a thickness of 10 μm was prepared and then attached to a slide glass, and the antigen was activated. The intestinal organoid was blocked with a 5% FBS solution for 30 minutes, and a primary antibody was reacted at 4° C. overnight. Thereafter, the slide glass was washed, a secondary antibody was reacted at room temperature for 1 hour, and 4',6-diamidino-2-phenylindole (DAPI) was used as a nuclear staining reagent. Encapsulation operation was performed, and fluorescence was observed with a Zeiss LSM510 confocal laser microscope.

(10) Observation with Transmission Electron Microscope

After completion of differentiation induction, the intestinal organoid was prefixed with 2.5% glutaraldehyde and incubated overnight at 4° C. Thereafter, post-fixation was performed with 1% osmium tetroxide at 4° C. for 2 hours, and dehydration operation with ethanol was performed. After substitution with propylene oxide, the intestinal organoid was embedded in the resin. A 0.1-μm section was prepared and subjected to electron staining with uranyl acetate, and then microvilli and tight junctions were observed with a JEM-1400 Plus transmission electron microscope.

(11) Permeation Experiment of FITC-Dextran 4000 (FD-4)

After completion of differentiation induction, the intestinal organoid was incubated at 37° C. with HBSS (Hanks buffered saline solution) containing FITC-dextran 4000 (FD-4). Used was HBSS having a pH of 7.4 and containing 137 mmol/L sodium chloride, 5.4 mmol/L potassium chloride, 0.81 mmol/L magnesium sulfate, 0.44 mmol/L potassium dihydrogen phosphate, 0.34 mmol/L disodium hydrogen phosphate, 1.3 mmol/L calcium chloride, 4.2 mmol/L sodium hydrogen carbonate, 5.6 mmol/L D-glucose, and 10 mmol/L HEPES. After completion of incubation, the cells were washed with ice-cooled HBSS. Thereafter, fluorescence was observed with a Nikon ECLIPSE Ti-S microscope.

(12) Rhodamine 123 Uptake Experiment

After completion of differentiation induction, the intestinal organoid was incubated with HBSS containing rhodamine 123 at 37° C. After completion of incubation, the cells were washed with ice-cooled HBSS to stop uptake. Thereafter, fluorescence was observed with a Zeiss LSM510 confocal laser microscope.

(13) Drug Metabolism Experiment

After completion of differentiation induction, the intestinal organoid was incubated in a medium containing 5 μmol/L midazolam (Advanced-DMEM/F12 containing 2 mmol/L L-Glu, 2% B27 supplement, 1% N2 supplement, 100 units/mL penicillin G, and 100 μg/mL streptomycin) at 37° C. After the elapse of 24 hours, the medium was sampled. The metabolic activity was calculated from the amount of midazolam 1-hydroxide in the medium measured using a liquid chromatography-mass spectrometer (LC-MS/MS). After completion of the metabolism experiment, protein quantification was performed, and the metabolic activity was corrected by the amount of protein.

The characteristics of the marker genes used in this study are shown below.

α-SMA (alpha-smooth muscle actin. smooth muscle marker)

ABCB1/MDR1 (ATP binding cassette transporter B1/multidrug resistant protein 1; P-glycoprotein; efflux transporter)

ABCC2/MRP2 (ATP binding cassette transporter C2/multidrug resistance-related protein 2; efflux transporter)

ABCG2/BCRP (ATP binding cassette transporter G2/breast cancer resistant protein; efflux transporter)

CDX2 (Caudal-type homeo box 2; transcription factor involved in proliferation/differentiation of intestinal epithelial cells)

Chromogranin A (specific protein present in secretory granules; intestinal endocrine cell marker)

CYP3A4 (cytochrome P450 3A4; main drug metabolizing enzyme in the human small intestine)

CYP3A8 (cytochrome P450 3A8; main drug-metabolizing enzyme in the cynomolgus monkey small intestine)

E-cad (E-cadherin) (epithelial cadherin; a group of glycoproteins present on the cell surface which are molecules responsible for cell adhesion)

LGR5 (G protein-coupled receptor containing leucine-rich repeats; intestinal stem cell marker)

Lysozyme (enzyme hydrolyzing the polysaccharide making up the cell walls of eubacteria; intestinal Paneth's cell marker)

MUC2 (mucin 2 glycoprotein; goblet cell marker)

Occludin (main protein involved in the formation of tight junctions)

OLFM4 (Olfactomedin 4; intestinal stem cell marker)

SLC15A1/PEPT1 (SLC (solute carrier) family member 15A1/peptide transporter 1; expressed on the apical membrane side of the small intestine)

SLCO2B1/OATP2B1 (SLC (solute carrier) organic anion transporter 2B1; expressed on the apical membrane side of the small intestine)

Villin (main constituent of microvilli; absorptive epithelial cell marker)

Vim (Vimentin; intermediate filament unique to mesenchymal cells)

2. Results and Discussion (1) Induction of Differentiation into Intestinal Organoids Using Low Molecular Weight Compounds (FIG. 1)

The effects of the low molecular weight compounds added during induction of differentiation from human and cynomolgus monkey iPS cells into intestinal organoids were investigated. As a result, the mRNA expression level of various pharmacokinetics-related genes including intestinal tract-related genes and CYP3A increased in the group (A/PD/5-aza) to which A-83-01 (0.5 μmol/L), PD98059 (20 μmol/L), and 5-aza-2'-deoxycytidine (5 won) were added. In the group (A/PD/5-aza/DAPT) to which DAPT (5 μmol/L) was further added, the mRNA expression of many pharmacokinetics-related genes increased in the human intestinal organoids, for example, about 2,000 times for cytochrome P450 (CYP) 3A4 as the main drug metabolizing enzyme in the intestinal tracts; about 10 times for SLC15A1/PEPT1 as a peptide uptake transporter; and about 36 times for ABCB1/MDR1, about 125 times for ABCG2/BCRP, and about 47 times for ABCC2/MRP2 as an efflux transporter, as compared with the case of the control group. In addition, the markers of cells which compose the intestinal tract, such as Villin (absorptive epithelial cells), MUC2 (goblet cells), Chromogranin A (intestinal endocrine cells), CDX2 (cells of the intestinal lineage), and LGR5 (intestinal stem cells) showed similar or higher mRNA expression, as compared with the case of the control group. A similar tendency as in the human intestinal organoids was exhibited in the cynomolgus monkey intestinal organoids, and the mRNA expression of many pharmacokinetic-related genes increased, for example, about 1,400 times for CYP3A8; about 2,200 times for SLC15A1/PEPT1; and about 18 times for ABCB1/MDR1, about 2.8 times for ABCG2/BCRP, and about 27 times for ABCC2/MRP2, as compared with the case of the control group. In addition, Villin, MUC2, Chromogranin A, Lysozyme, and CDX2 showed similar or higher mRNA expression, as compared with the case of the control group. Therefore, in the subsequent experiments, A-83-01, PD98059, 5-aza-2'-deoxycytidine, and DAPT were added for differentiation, and the analysis proceeded.

(2) Morphological Observation of Human and Cynomolgus Monkey Intestinal Organoids Obtained by Differentiation Induction Using Novel Combination of Low Molecular Weight Compounds The human and cynomolgus monkey iPS cell-derived intestinal organoids obtained by differentiation induction using the novel combination of low molecular weight compounds had a spherical shape (FIGS. 2A and 2B). From the observation with a transmission electron microscope, the formation of microvilli and tight junctions present on the intestinal brush border membrane side was confirmed inside the intestinal organoids (FIGS. 2C and 2D). In addition, the results of HE staining and Alcian blue staining revealed that the intestinal organoids constitute a cell population containing secretory cells (FIGS. 2E to 2J).

(3) Immunofluorescence Staining of Human and Cynomolgus Monkey Intestinal Organoids Obtained by Differentiation Induction Using Novel Combination of Low Molecular Weight Compounds By immunofluorescence staining, the expression of markers of various cells constituting the intestinal tract (absorptive epithelial cells, intestinal stem cells, goblet cells, intestinal endocrine cells, Paneth's cells, mesenchymal cells) was observed (FIG. 3). Therefore, it was suggested that the intestinal organoids were intestinal tissue analogs containing these cells.

(4) Formation of Tight Junctions of Human and Cynomolgus Monkey Intestinal Organoids Obtained by Differentiation Induction Using Novel Combination of Low Molecular Weight Compounds and their Function To confirm whether functional tight junctions were formed, protein expression of Occludin as a tight junction marker was first confirmed by immunofluorescence staining (FIGS. 4A to 4C). From this result, it was suggested that the tight junction was expressed along the luminal side of the intestinal organoids. Also, the observation with a transmission electron microscope revealed that the lumen inside of the intestinal organoids corresponds to the intestinal brush border membrane side (FIGS. 2C and 2D). Therefore, when a test on permeation into the intestinal organoids was performed using FITC-dextran 4000 (FD-4) as a non-absorbable marker, no accumulation in the organoids was observed (FIGS. 4D to 4G). From this result, it was suggested that functional tight junctions were formed in the human and cynomolgus monkey intestinal organoids obtained by differentiation induction using the novel combination of low molecular weight compounds.

Figures 1, 2, 3, 4, 5:
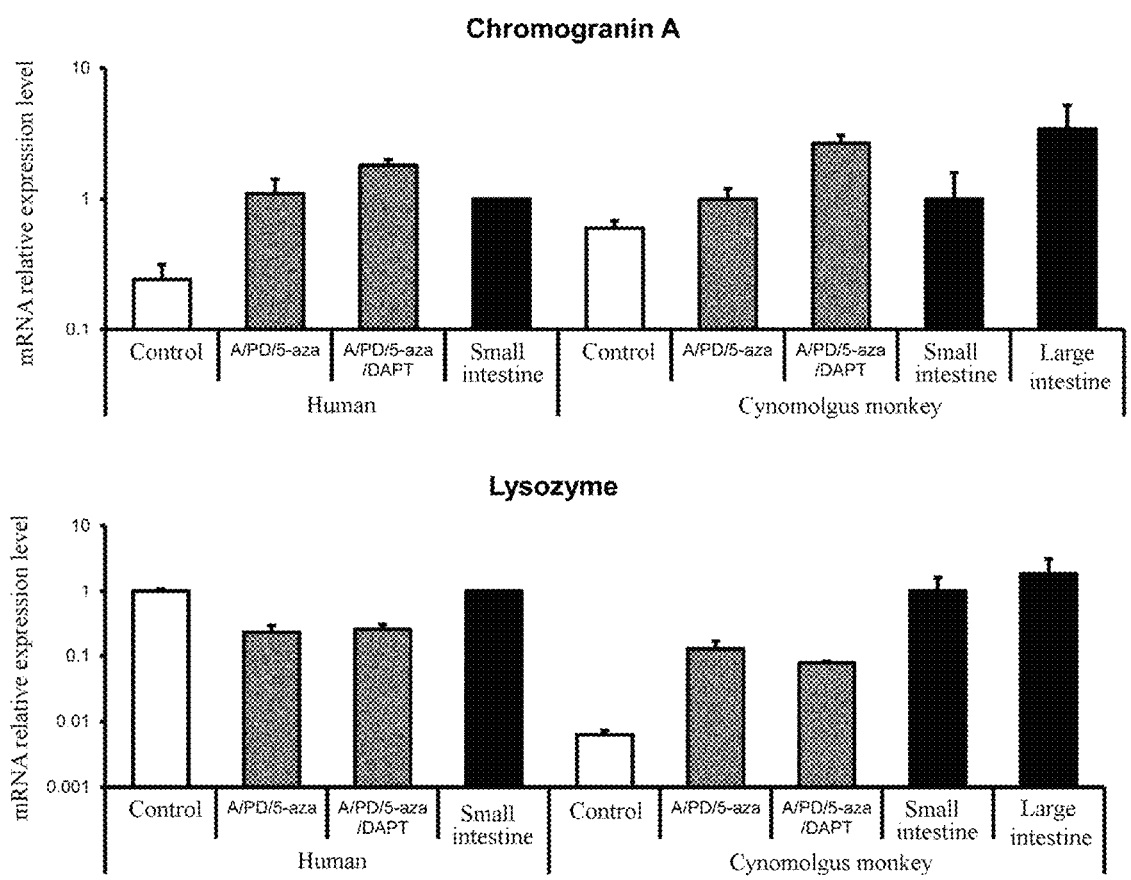

(5) Immunofluorescence Staining of Transporters of Human and Cynomolgus Monkey Intestinal Organoids Obtained by Differentiation Induction Using Novel Combination of Low Molecular Weight Compounds In the human and cynomolgus monkey intestinal organoids obtained by differentiation induction using the novel combination of low molecular weight compounds, protein expression of SLC15A1/PEPT1, which is specifically expressed in the small intestine, and ABCB1/MDR1, which is a major excretion transporter in the intestinal tracts, was found along the inner lumen of the intestinal organoids (FIG. 5).

Figures 1, 2, 3, 4, 5, 6:
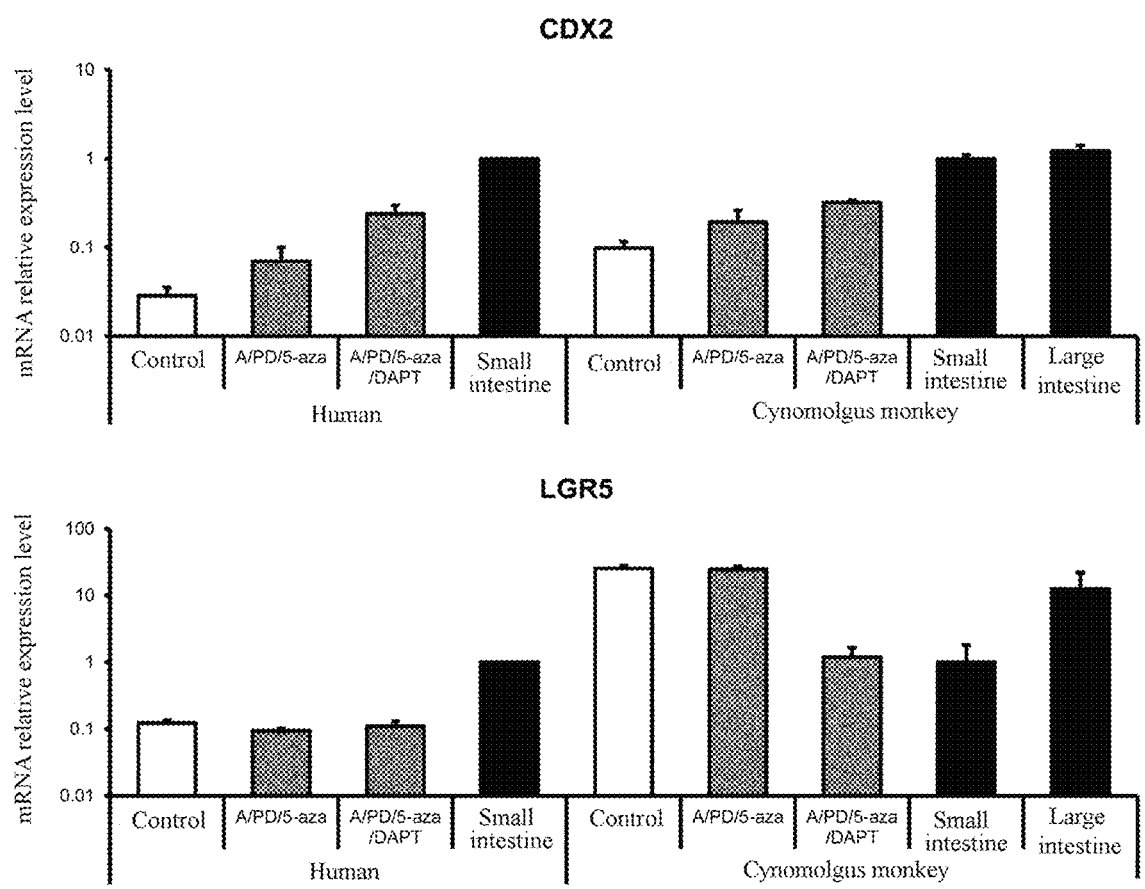

(6) Evaluation of Function of ABCB1/MDR1 Using Rhodamine 123 of Human Intestinal Organoids Obtained by Differentiation Induction Using Novel Combination of Low Molecular Weight Compounds The function of ABCB1/MDR1 was evaluated using rhodamine 123 as a substrate of ABCB1/MDR1 as an efflux transporter and verapamil as an inhibitor. Excretion of rhodamine 123 into the intestinal organoids was observed (FIGS. 6A and 6B), and transport in the excretion direction was significantly suppressed by verapamil (FIGS. 6C and 6D). This suggested that the human intestinal organoids obtained by differentiation induction using the novel combination of low molecular weight compounds had the function of ABCB1/MDR1.

Figures 1, 2, 3, 4, 5, 6, 7:
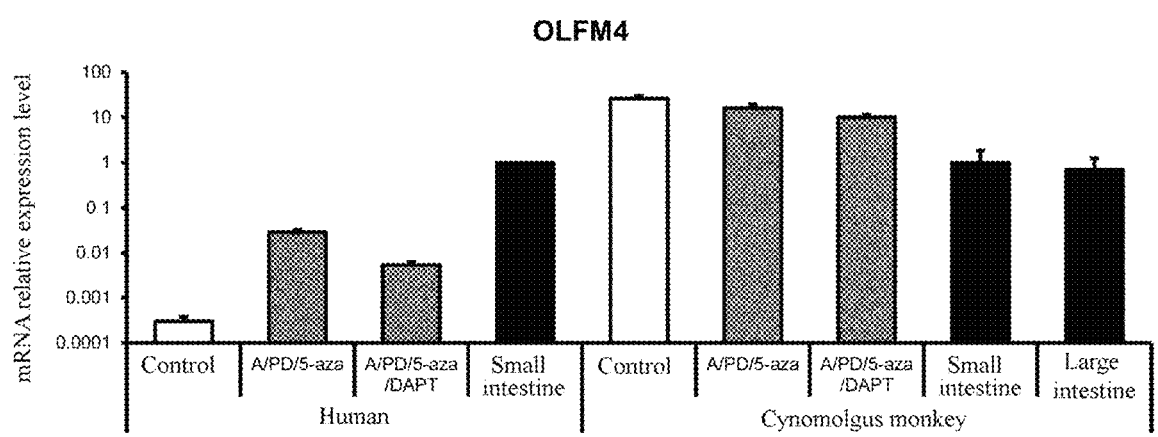
Figure 2:
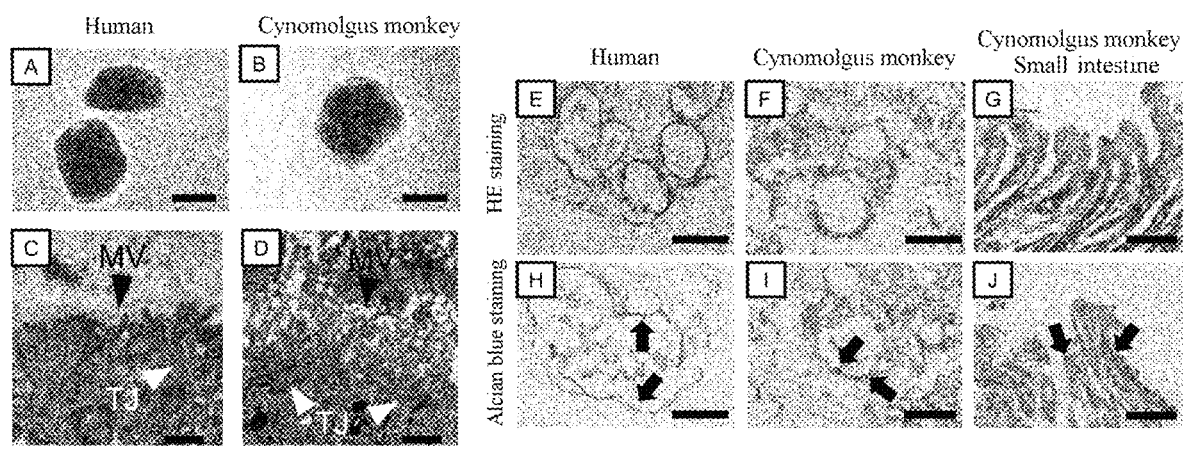
Figure 3:
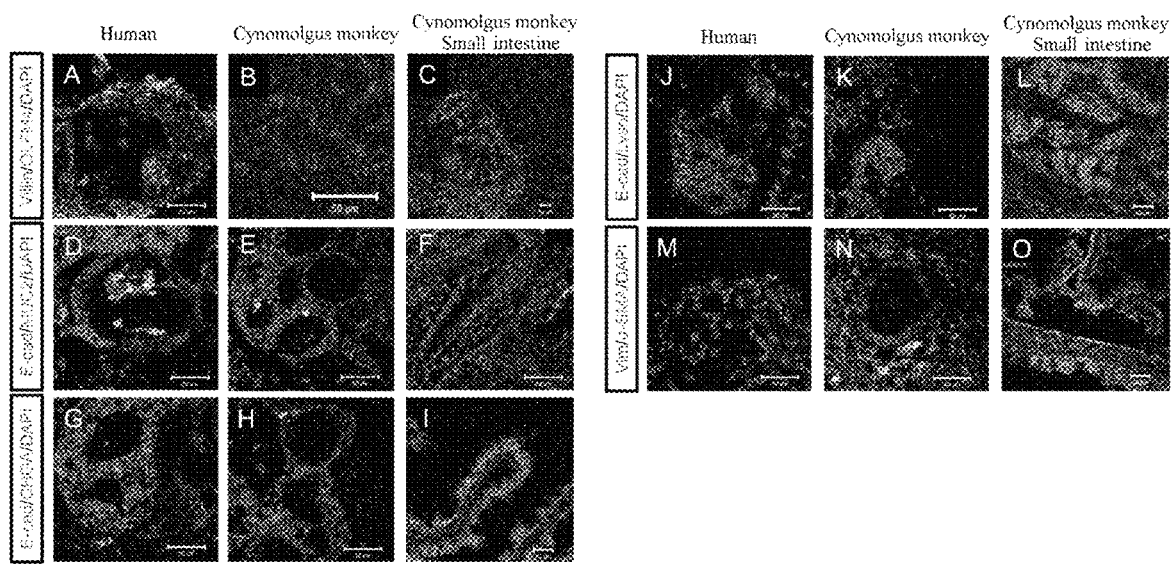
Figure 4:
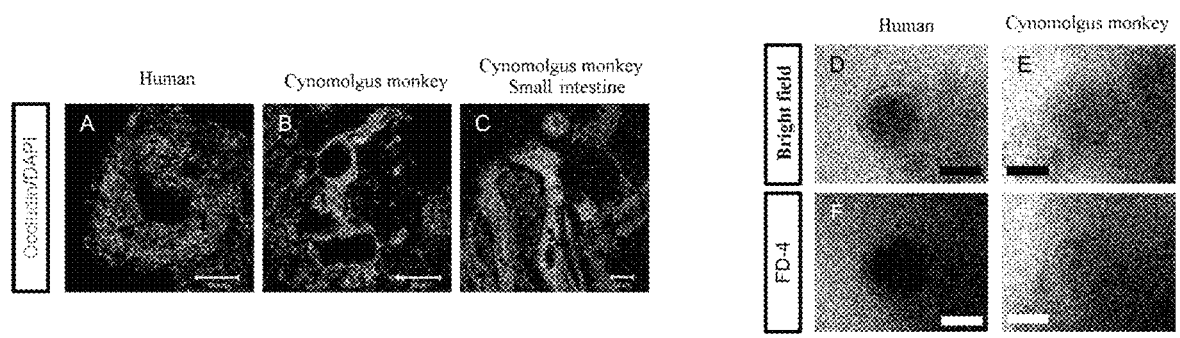
Figure 5:
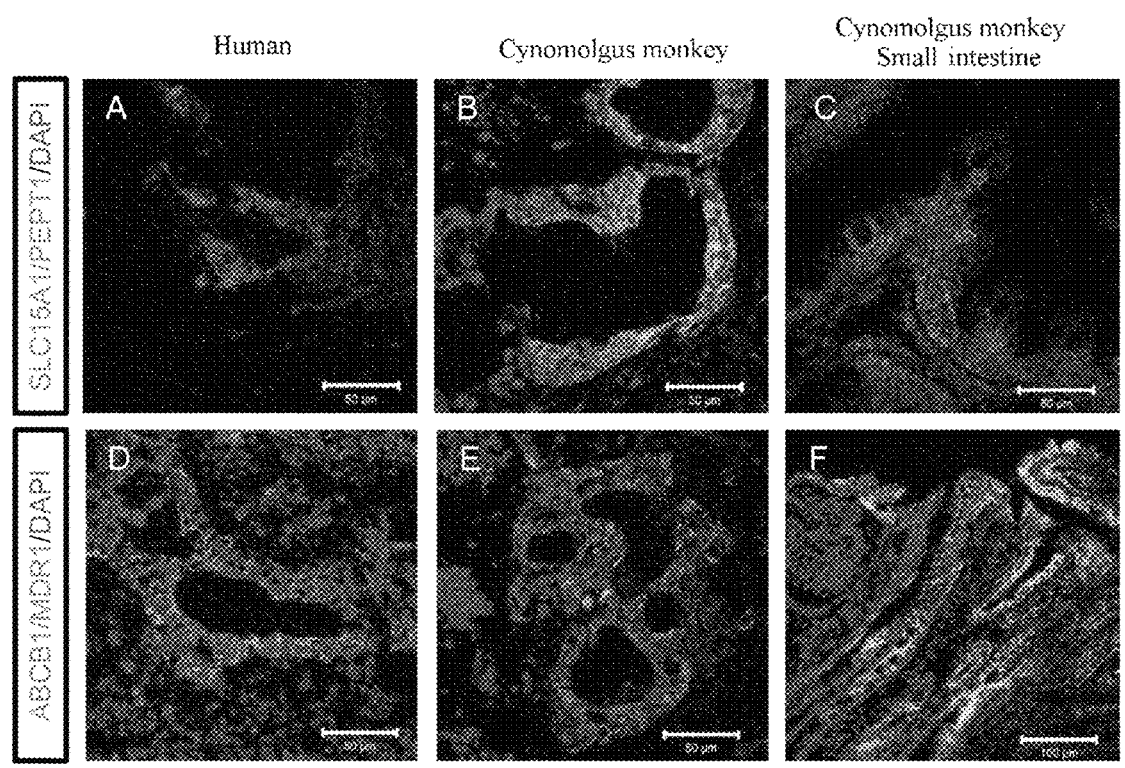
Figure 6:
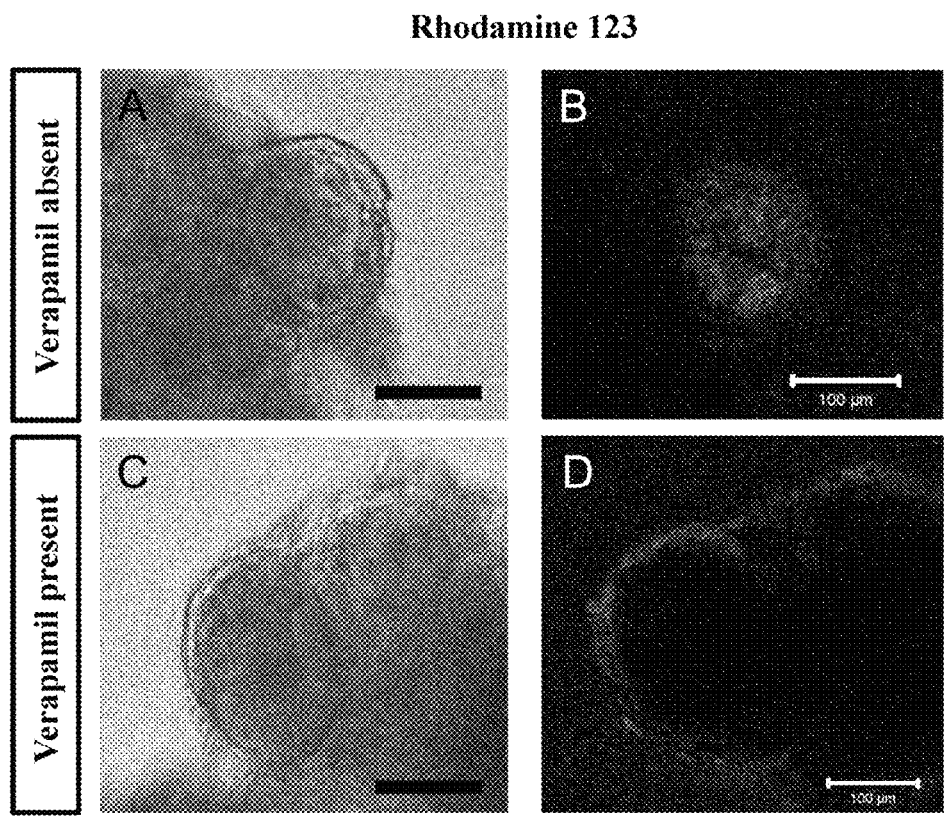
Figure 7:
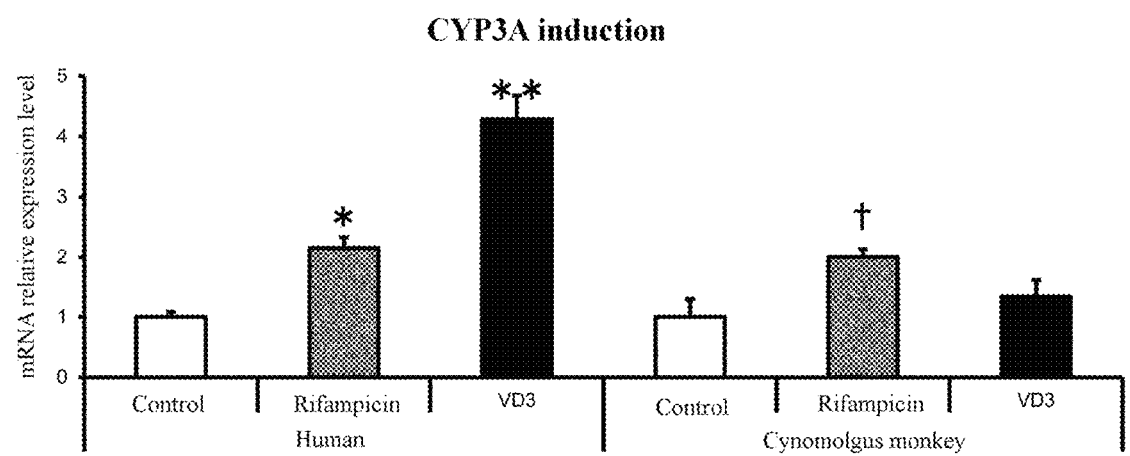

(7) CYP3A induction ability of human and cynomolgus monkey intestinal organoids obtained by differentiation induction using novel combination of low molecular weight compounds The induction of the mRNA expression of CYP3A was examined using rifampicin and 1α, 25-dihydroxyvitamin $D_3$ (VD3) as CYP3A inducers. In the human intestinal organoids, the mRNA expression of CYP3A4 was significantly induced approximately twice in the rifampicin-added group and approximately 4.5 times in the VD3-added group, as compared with the control group (FIG. 7). This suggested that the human intestinal organoids obtained by differentiation induction using the novel combination of low molecular weight compounds had drug responsiveness of CYP3A. In the cynomolgus monkey intestinal organoids, the mRNA expression of CYP3A8 was significantly induced approximately twice in the rifampicin-added group as compared with the control group, but no induction of the mRNA expression of VD3 was observed (FIG. 7).

(8) CYP3A8 Metabolic Activity of Cynomolgus Monkey Intestinal Organoids Obtained by Differentiation Induction Using Novel Combination of Low Molecular Weight Compounds The CYP3A8 metabolic activity was evaluated using midazolam as a substrate of human CYP3A4 and cynomolgus monkey CYP3A8, and ketoconazole as an inhibitor thereof. In the cynomolgus monkey intestinal organoids, the midazolam metabolic activity was observed, and its activity was significantly inhibited to about one-twentieth by the addition of ketoconazole (FIG. 8). Thus, it was suggested that the cynomolgus monkey intestinal organoids obtained by differentiation induction using the novel combination of low molecular weight compounds had the CYP3A8 metabolic capacity.

3. Conclusion

From the above results, a combination of low molecular weight compounds useful for promoting the differentiation from human and cynomolgus monkey iPS cells into intestinal organoids was newly found in this study. In addition, it was revealed that the intestinal organoids prepared by this method have various pharmacokinetic functions characteristic of the intestinal tracts, such as drug metabolizing enzyme activity and induction ability, in addition to functional tight junctions and transport functions of the efflux transporter.

<Study on Suspension Culture Conditions>

For the purpose of promoting differentiation, acquiring higher functions, and constructing a culture system that does not use heterologous animal-derived ingredients, suspension culture was performed using a medium that used a polysaccharide polymer as an alternative to Matrigel when preparing intestinal organoids.

1. Method (1) Cells

Human iPS cells (iPS-51: Windy) were prepared by introducing octamer binding protein 3/4 (OCT3/4), sex determining region Y-box 2 (SOX2), kruppel-like factor 4 (KLF4), and v-myc myelocytomatosis viral oncogene homolog (avian) (c-MYC) into human fetal lung fibroblasts MRC-5 using a pantropic retrovirus vector and then cloning human ES cell-like colonies, and were provided by Dr. Akihiro Umezawa, National Center for Child Health and Development. Mouse embryonic fibroblasts (MEFs) were used as feeder cells.

(2) Medium

A Dulbecco's modified eagle medium (DMEM) containing 10% fetal bovine serum (FBS), 2 mmol/L L-glutamine (L-Glu), 1% non-essential amino acid (NEAA), 100 units/mL penicillin G, and 100 μg/mL streptomycin was used for culture of MEF. As an MEF stripping solution, used was 0.05% trypsin-ethylenediaminetetraacetic acid (EDTA). Cell Banker 1 was used as an MEF preservation solution. DMEM Ham's F-12 (DMEM/F12) containing 20% knockout serum replacement (KSR), 0.8% NEAA, 2 mmol/L L-Glu, 0.1 mmol/L 2-mercaptoethanol (2-MeE), and 5 ng/mL fibroblast proliferation factor (FGF) 2 was used for maintenance culture of the human iPS cells. Dulbecco's phosphate buffered saline (PBS) containing 1 mg/mL collagenase IV, 0.25% trypsin, 20% KSR, and 1 mmol/L calcium chloride was used as the stripping solution for the human iPS cells. As a preservation solution for human iPS cells, a cryopreservation solution for primate ES/iPS cells was used.

(3) Culture of Human iPS Cells

The human iPS cells were seeded on MEF ($6 \times 10^5$ cells/100 mm dish) treated with mitomycin C, and cultured at 37° C. in a $CO_2$ incubator under the 5% $CO_2$/95% air condition. The human iPS cells were subcultured at a split ratio of 1:2 to 1:3 after 3 to 5 days of culture. For human iPS cells, the medium was exchanged 48 hours after thawing and thereafter daily.

(4) Differentiation of Human iPS Cells into Intestinal Organoids

The human iPS cells were seeded in a culture dish coated with Matrigel diluted 30-fold with growth factors removed in a culture medium for human iPS cells at the time of subculture, and cultured in a StemSure (registered trademark) hPSC medium containing 35 ng/mL FGF2. The differentiation of the human iPS cells into intestinal organoids started in a state in which the proportion of undifferentiated colonies arrived at about 80%. The iPS cells were cultured in a Roswell Park Memorial Institute (RPMI) medium containing 100 ng/mL activin A, 100 units/mL penicillin G, 100 μg/mL streptomycin, and 2 mmol/L L-Glu for 1 day, an RPMI medium containing 0.2% FBS, 100 ng/mL activin A, 100 units/mL penicillin G, 100 μg/mL streptomycin, and 2 mmol/L L-Glu for 1 day, and an RPMI medium containing 2% FBS, 100 ng/mL activin A, 100 units/mL penicillin G, 100 μg/mL streptomycin, and 2 mmol/L L-Glu for 1 day to be differentiated into the endoderm. Then, the cells were differentiated into intestinal stem cells by culturing the iPS cells in an RPMI+glutamax medium containing 2% FBS, 500 ng/mL FGF4, 3 μmol/L CHIR99021, 100 units/mL penicillin G, and 100 μg/mL streptomycin for 4 days. After treatment with FGF4 and CHIR99021, Y-27632 (Rho-binding kinase inhibitor) was added so as to attain 10 μmol/L, and cells treated under the 5% $CO_2$/95% air condition for 60 minutes at 37° C. in a $CO_2$ incubator were stripped with 0.05% trypsin-EDTA. The cell mass was crushed with a 40-μm nylon mesh cell strainer, and $3.0 \times 10^6$ cells were seeded on 100-mm EZSPHERE (registered trademark). Then, the cells were cultured in Advanced-DMEM/F12 containing 2 mmol/L L-Glu, 2% B27 supplement, 1% N2 supplement, 100 units/mL penicillin G, 100 μg/mL streptomycin, 100 ng/mL epidermal growth factor (EGF), 100 ng/mL Noggin, 200 ng/mL R-spondin-1, and 10 μmol/L Y-27632 for 3 days, and then cultured in suspension on an ultra-low adhesion 6-well plate in Advanced-DMEM/F12 containing 2 mmol/L L-Glu, 2% B27 supplement, 1% N2 supplement, 100 units/mL penicillin G, 100 μg/mL streptomycin, 100 ng/mL EGF, 100 ng/mL Noggin, 200 ng/mL R-spondin-1, and 3% Matrigel with growth factors removed or polysaccharide polymer (deacylated gellan gum) for 24 days to be differentiated into intestinal organoids. Furthermore, from Days 19 to 34 from the start of differentiation, 5 μmol/L N-[(3,5-difluorophenyl)acetyl]-L-alanyl-2-phenyl-1,1-dimethylethyl ester-glycine (DAPT) was added, in addition to PD98059 (20 μmol/L), 5-aza-2'-deoxycytidine (5 μmol/L), and A-83-01 (0.5 μmol/L) as our previously found low molecular weight compounds. The treatment of the drug-metabolizing enzyme with the inducer was performed by adding 1α, 25-dihydroxyvitamin $D_3$ (VD3) to attain 1 μmol/L to Advanced-DMEM/F12 containing 2 mmol/L L-Glu, 2% B27 supplement, 1% N2 supplement, 100 units/mL penicillin G, 100 μg/mL streptomycin, 100 ng/mL EGF, 100 ng/mL Noggin, 200 ng/mL R-spondin-1, and 3% Matrigel with growth factors removed or polysaccharide polymer (deacylated gellan gum), followed by culture for 72 hours before recovery. As the polysaccharide polymer, used was FP001 or FP003 provided by Nissan Chemical Industries, Ltd. at a concentration of 0.015% (w/v) in the medium, and the effects thereof on differentiation into intestinal organoids were examined.

(5) Extraction of Total Ribonucleic Acid (RNA)

Total RNA was extracted according to the attached manual of Agencourt RNAdvence Tissue after end of differentiation induction of human iPS cells.

(6) Reverse Transcription Reaction

Complementary DNA (cDNA) was synthesized using ReverTra Ace qPCR RT Master Mix according to the attached manual.

(7) Real-Time RT-PCR Method

For Real-Time RT-PCR, KAPA SYBR Fast qPCR Kit was used, and the cDNA was used as a template. The reaction was performed according to the attached manual. The results were corrected using hypoxanthine phosphoribosyltransferase (HPRT) as an endogenous control.

(8) Hematoxylin-Eosin (HE) Staining

After completion of differentiation induction, the intestinal organoid was fixed with 4% paraformaldehyde, and frozen and embedded with an OCT compound. A frozen section having a thickness of 10 µm was prepared and then attached to a slide glass. Staining was performed using Mayer's hematoxylin and eosin alcohol.

(9) Immunofluorescence Staining

After completion of differentiation induction, the intestinal organoid was fixed with 4% paraformaldehyde, and frozen and embedded with an OCT compound. A frozen section having a thickness of 10 µm was prepared and then attached to a slide glass, and the antigen was activated. The intestinal organoid was blocked with a 5% FBS solution for 30 minutes, and a primary antibody was reacted at 4° C. overnight. Thereafter, the slide glass was washed, a secondary antibody was reacted at room temperature for 1 hour, and 4',6-diamidino-2-phenylindole (DAPI) was used as a nuclear staining reagent. Encapsulation operation was performed, and fluorescence was observed with a Zeiss LSM510 confocal laser microscope.

(10) Rhodamine 123 Transport Experiment

After completion of differentiation induction, the intestinal organoid was incubated with HBSS containing rhodamine 123 at 37° C. Used was HBSS having a pH of 7.4 and containing 137 mmol/L sodium chloride, 5.4 mmol/L potassium chloride, 0.81 mmol/L magnesium sulfate, 0.44 mmol/L potassium dihydrogen phosphate, 0.34 mmol/L disodium hydrogen phosphate, 1.3 mmol/L calcium chloride, 4.2 mmol/L sodium hydrogen carbonate, 5.6 mmol/L D-glucose, and 10 mmol/L HEPES. After completion of incubation, the cells were washed with ice-cooled PBS to stop uptake. Rhodamine 123 was released out of the organoids by incubation in PBS warmed to 37° C. for 4 hours. Thereafter, the fluorescence intensity of the supernatant was measured using a Synergy HTX microplate reader. After completion of the transport experiment, protein quantification was performed, and the fluorescence intensity was corrected by the amount of protein.

(11) Hoechst 33342 Transport Experiment

After completion of differentiation induction, the intestinal organoid was incubated with HBSS containing Hoechst 33342 at 37° C. After completion of incubation, the cells were washed with ice-cooled PBS to stop uptake. Hoechst 33342 was released out of the organoids by incubation in PBS warmed to 37° C. for 4 hours. Thereafter, the fluorescence intensity of the supernatant was measured using a Synergy HTX microplate reader. After completion of the transport experiment, protein quantification was performed, and the fluorescence intensity was corrected by the amount of protein.

(12) Drug Metabolism Experiment

After completion of differentiation induction, the intestinal organoid was incubated in a medium containing 5 µmol/L midazolam (Advanced-DMEM/F12 containing 2 mmol/L L-Glu, 2% B27 supplement, 1% N2 supplement, 100 units/mL penicillin G, and 100 µg/mL streptomycin) at 37° C. After the elapse of 24 hours, the medium was sampled. The metabolic activity was calculated from the amount of midazolam 1-hydroxide in the medium measured using a liquid chromatography-mass spectrometer (LC-MS/MS). After completion of the metabolism experiment, protein quantification was performed, and the metabolic activity was corrected by the amount of protein.

In this study, the following marker genes: a-SMA, ABCB1/MDR1, ABCG2/BCRP, CDX2, Chromogranin A, CYP3A4, E-cad (E-cadherin), Ki67 (expressed in cells during the G1, S, G2, and M phases; proliferating cell marker), LGR5, Lysozyme, MUC2, Occludin, OLFM4, PXR (pregnane X receptor; nuclear receptors involved in transcriptional regulation such as CYP3A4), Sucrase-isomaltase (transmembrane type II glycoprotein; expressed at the brush border of the intestinal epithelial cells), SLC15A1/PEPT1, Villin, and Vim (Vimentin) were used.

2. Results and Discussion (1) Induction of Differentiation into Human Intestinal Organoids Using Polysaccharide Polymer The effects of the polysaccharide polymer added during induction of differentiation from human iPS cells into intestinal organoids were investigated. As a result, in the group to which FP001 or FP003 was added, the mRNA expression levels of various pharmacokinetic-related genes including intestinal tract-related genes and CYP3A increased. The mRNA expression of many pharmacokinetics-related genes increased, for example, about 3.7 times for cytochrome P450 (CYP) 3A4 as the main drug metabolizing enzyme in the intestinal tracts; about 4.1 times for SLC15A1/PEPT1 as a peptide uptake transporter; and about 4.5 times for ABCB1/MDR1 as an efflux transporter, especially in the group to which FP001 was added, as compared with the control group to which 3% Matrigel with growth factors removed was added. In addition, cell markers making up the intestinal tract, such as Villin (absorptive epithelial cells), sucrase-isomaltase (brush border of epithelial cells), MUC2 (goblet cells), and LGR5 (intestinal stem cells) showed similar or higher mRNA expression, as compared with the case of the control group. (FIG. 10)

(2) Morphological Observation of Human Intestinal Organoids Obtained by Differentiation Induction Using Polysaccharide Polymers Human iPS cell-derived intestinal organoids obtained by differentiation induction using Matrigel and polysaccharide polymers had a spherical shape (FIGS. 11A to 11C). From the results of HE staining, lumens were confirmed also in human intestinal organoids obtained by differentiation induction using polysaccharide polymers (FIGS. 11D to 11F).

(3) Immunofluorescence Staining of Human Intestinal Organoids Obtained by Differentiation Induction Using Polysaccharide Polymers Immunofluorescence staining revealed expression of various cells constituting the intestinal tracts (absorptive epithelial cells, intestinal stem cells, goblet cells, intestinal endocrine cells, Paneth's cells, mesenchymal cells), efflux transporters and tight junction markers (FIG. 12). Therefore, it was suggested that the intestinal organoids were intestinal tissue analogs containing these cells.

(4) Evaluation of Function of ABCB1/MDR1 Using Rhodamine 123 of Human Intestinal Organoids Obtained by Differentiation Induction Using Polysaccharide Polymers The function of ABCB1/MDR1 was evaluated using rhodamine 123 as a substrate of ABCB1/MDR1 as an efflux transporter and verapamil as an inhibitor. Excretion of rhodamine 123 into the intestinal organoids was observed, and transport in the excretion direction was suppressed by verapamil (FIG. 13). This suggested that the human intestinal organoids obtained by differentiation induction using polysaccharide polymers had the function of ABCB1/MDR1.

(5) Evaluation of Function of ABCG2/BCRP Using Hoechst 33342 of Human Intestinal Organoids Obtained by Differentiation Induction Using Polysaccharide Polymers The function of ABCG2/BCRP was evaluated using Hoechst 33342 as a substrate of ABCG2/BCRP as an efflux transporter and Ko143 as an inhibitor. Excretion of Hoechst 33342 into the intestinal organoids was observed, and transport in the excretion direction was suppressed by Ko143 (FIG. 14). This suggested that the human intestinal organoids obtained by differentiation induction using polysaccharide polymers had the function of ABCG2/BCRP.

(6) CYP3A4 Induction Ability of Human Intestinal Organoids Obtained by Differentiation Induction Using Polysaccharide Polymers The induction of the mRNA expression of CYP3A4 was examined using 1α, 25-dihydroxyvitamin $D_3$ (VD3) as a CYP3A inducer. As compared with the control group, the mRNA expression of CYP3A4 was significantly induced in the VD3-added group (FIG. 15A). Further, in the VD3-added group, the midazolam metabolic activity was significantly increased (FIG. 15B), and induction, at the protein level, of CYP3A4 was observed. This suggested that the human intestinal organoids obtained by differentiation induction using polysaccharide polymers had the drug responsiveness of CYP3A4.

(7) CYP3A4 Metabolic Activity of Human Intestinal Organoids Obtained by Differentiation Induction Using Polysaccharide Polymers The CYP3A4 metabolic activity was evaluated using midazolam as a substrate of CYP3A4 and ketoconazole as an inhibitor thereof. In the human intestinal organoids, the midazolam metabolic activity was observed, and its activity was significantly inhibited by the addition of ketoconazole (FIG. 16). Thus, it was suggested that the human intestinal organoids obtained by differentiation induction using polysaccharide polymers had the CYP3A4 metabolic capacity.

3. Conclusion

From the above results, a floating agent (viscous material) useful for the differentiation from human iPS cells into intestinal organoids was newly found in this study. In addition, it was revealed that the intestinal organoids prepared by this method have various pharmacokinetic functions characteristic of the intestinal tracts, such as drug metabolizing enzyme activity and induction ability, in addition to transport functions of the efflux transporter. Furthermore, FP001 and FP003 are polysaccharide polymers and do not contain ingredients derived from heterologous animals, and thus are considered to be extremely useful as culture materials used when intestinal organoids are used in regenerative medicine.

INDUSTRIAL APPLICABILITY

The present invention enables the preparation of a functional intestinal organoid. The combination of factors employed in the present invention (a MEK1/2 inhibitor, a DNA methylation inhibitor, a TGF-β receptor inhibitor, and a γ-secretase inhibitor) is composed of low molecular weight compounds that are inexpensive and have little lot-to-lot difference. This feature is extremely important from the practical viewpoint, and the present invention provides, for example, a reduction in preparation cost for the intestinal organoid and improvement in quality and reliability of the intestinal organoid. The intestinal organoid prepared by the present invention is functional structures and can be expected to be applied to various uses. For example, they can be utilized for in vitro evaluation systems (evaluation of drug efficacy, toxicity and pharmacokinetics), preparation of intestinal pathological models such as intractable inflammatory bowel diseases and elucidation of a pathological mechanism using them, and transplantation into living bodies (humans, experimental animals, and the like).

The present invention is not limited to the description of the embodiments and examples of the present invention at all. Various modifications that can be easily achieved by those skilled in the art without departing from the claims also fall within the scope of the present invention. The contents of the articles, the patent laid-open publications, patent publications, and the like specified herein shall be cited by incorporation in their entity.

The invention claimed is:

1. A method for preparing an intestinal organoid from pluripotent stem cells, comprising the following steps (1) to (4):
    (1) differentiating pluripotent stem cells into endoderm-like cells;
    (2) differentiating the endoderm-like cells obtained in step (1) into intestinal stem cell-like cells;
    (3) culturing the intestinal stem cell-like cells obtained in step (2) to form spheroids; and
    (4) differentiating the spheroids formed in step (3) to form an intestinal organoid, the step including culture in the presence of a MEK1/2 inhibitor, a DNA methylation inhibitor, a TGF-β receptor inhibitor, and a γ-secretase inhibitor, in addition to an epidermal growth factor, a BMP inhibitor, and a Wnt signal activator,
    wherein step (4) includes the following steps (4-1) and (4-2):
    (4-1) culture in the presence of the epidermal growth factor, the BMP inhibitor, and the Wnt signal activator; and
    (4-2) culture in the presence of the MEK1/2 inhibitor, the DNA methylation inhibitor, the TGF-β receptor inhibitor, and the γ-secretase inhibitor, in addition to the epidermal growth factor, the BMP inhibitor, and the Wnt signal activator;
    wherein step (4-1) precedes step (4-2).

2. The preparation method according to claim 1, wherein the pluripotent stem cells are induced pluripotent stem cells or embryonic stem cells.

3. The preparation method according to claim 1, wherein the pluripotent stem cells are human or primate cells.

4. The preparation method according to claim 1, wherein the pluripotent stem cells are human induced pluripotent stem cells, and wherein step (2) includes culture in the presence of FGF4 and a Wnt agonist.

5. The preparation method according to claim 4, wherein the human induced pluripotent stem cells are induced pluripotent stem cells derived from a patient with a bowel disease.

6. The preparation method according to claim 1, wherein the pluripotent stem cells are cynomolgus monkey induced pluripotent stem cells, and wherein step (2) includes culture in the presence of FGF2 and a GSK-3 inhibitor.

7. The preparation method according to claim 1, wherein, in the culture in step (3), a plurality of the spheroids are formed together by using a culture vessel in which a plurality of wells uniform in shape and size are formed in a low cell adhesive or non-cell adhesive culture surface.

8. The preparation method according to claim 1, wherein the BMP inhibitor is Noggin, and wherein the Wnt signal activator is R-spondin-1.

9. The preparation method according to claim 1, wherein the MEK1/2 inhibitor is PD98059, wherein the DNA methylation inhibitor is 5-aza-2'-deoxycytidine, wherein the TGF-β receptor inhibitor is A-83-01, and wherein the γ-secretase inhibitor is N-[(3,5-difluorophenyl) acetyl]-L-alanyl-2-phenyl-1,1-dimethylethyl ester-glycine.

10. The preparation method according to claim 1, wherein a liquid medium comprising a material that is able to form a three-dimensional network structure is used for the culture in step (4), and wherein a plurality of the spheroids formed in step (3) are cultured together in suspension.

11. The preparation method according to claim 10, wherein the material is one or more materials selected from the group consisting of polymer gels and polysaccharides.

12. The preparation method according to claim 10, wherein the material includes deacylated gellan gum.

13. The preparation method according to claim 1, wherein the culture period in step (4) is 12 days to 36 days.

14. The preparation method according to claim 1, wherein the culture period in step (4-1) is 3 days to 15 days, and wherein the culture period in step (4-2) is 3 days to 21 days.

* * * * *